(12) United States Patent
Wucherpfennig et al.

(10) Patent No.: US 8,314,210 B2
(45) Date of Patent: Nov. 20, 2012

(54) COMPOSITIONS AND METHODS FOR THE GENERATION OF MHC CLASS II COMPOUNDS BY PEPTIDE EXCHANGE

(75) Inventors: Kai W. Wucherpfennig, Brookline, MA (US); Nilufer Seth, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1235 days.

(21) Appl. No.: 10/617,568

(22) Filed: Jul. 11, 2003

(65) Prior Publication Data

US 2004/0197862 A1 Oct. 7, 2004

Related U.S. Application Data

(60) Provisional application No. 60/395,494, filed on Jul. 12, 2002, provisional application No. 60/397,893, filed on Jul. 22, 2002.

(51) Int. Cl.
*A61K 38/00* (2006.01)
*C07K 1/00* (2006.01)
*C07K 14/00* (2006.01)
*C07H 21/04* (2006.01)

(52) U.S. Cl. .......................... 530/345; 530/350; 530/402

(58) Field of Classification Search .......................... None
See application file for complete search history.

(56) References Cited

U.S. PATENT DOCUMENTS 5,820,866 A 10/1998 Kappler et al.
5,869,270 A 2/1999 Rhode et al.

FOREIGN PATENT DOCUMENTS

WO WO-01/70245 9/2001

OTHER PUBLICATIONS

Zhong et al (J. Exp. Med. 1996, 184: 2061-2066).*
DiBrino et al (J. Biol. Chem. 1994, 269(51): 32426-32434).*
Natarajan et al (J. Immunol. 1999, 162: 4030-4036).*
Zarutskie et al., "A Conformational Change in the Human Major Histocompatibility Complex Protin HLA-DR1 Induced by Peptide Binding," Biochemistry, 38:5878-5887 (1999).
Altman et al., "Phenotypic Analysis of Antigen-Specific T Lymphocytes," Science, 274:94-96 (1996).
Appel et al., "Kinetics of T-cell Receptor Binding by Bivalent HLA-DR-Peptide Complexes That Activate Antigen-specific Human T-cells," J. Biol. Chem., 275:312-321 (2000).
Appel et al., "Anergy Induction by Dimeric TCR Ligands," J. Immunol., 166:5279-5285 (2001).
Beckett et al., "A minimal peptide substrate in biotin holoenzyme synthetase-catalyzed biotinylation," Protein Sci., 8:921-929 (1999).
Crawford et al., "Detection of Antigen-Specific T Cells with Multivalent Soluble Class II MHC Covalent Peptide Complexes," Immunity, 8:675-682 (1998).

Eckels et al., "Human Helper T-Cell Clones That Recognize Different Influenza Hemagglutinin Determinants Are Restricted by Different HLA-D Region Epitopes," Immunogenetics, 19:409-423 (1984).
Frayser et al., "Empty and Peptide-Loaded Class II Major Histocompatibility Complex Proteins Produced by Expression in *Escherichia coli* and Folding in Vitro," Protein Expr. Purif., 15:105-114 (1999).
Garboczi et al., "HLA-A2-peptide complexes: Refolding and crystallation of molecules expressed in *Escherichia coli* and complexed with single antigenic peptides," Proc. Natl. Acad. Sci., USA, 89:3429-3433 (1992).
Gauthier et al., "Expression and crystallization of the complex of HLA-DR2 (DRA, DRB1*1501) and an immunodominant peptide of human myelin basic protein," Proc. Natl. Acad. Sci., USA, 95:11828-11833 (1998).
Halder et al., "Isolation of Novel HLA-DR Restricted Potential Tumor-associated Antigens from the Melanoma Cell Line FM3[1]," Cancer Res., 57:3238-3244 (1997).
Hammer et al., "Promiscuous and Allele-Specific Anchors in HLA-DR-Binding Peptides," Cell, 74:197-203 (1993).
Hausmann et al., "pH-dependent Peptide Binding Properties of the Type I Diabetes-associated I-A$^{g7}$ Molecule: Rapid Release of CLIP at an Endosomal pH," J. Exp. Med., 189:1723-1733 (1999).
Jensen et al., "Long-lived Complexes between Peptide and Class II Major Histocompatibility Complex Are Formed at Low pH with No Requirement for pH Neutralization," J. Exp. Med., 176:793-798 (1992).
Kalandadze et al., "Expression of Recombinant HLA-DR2 Molecules," J. Biol. Chem., 271:20156-20162 (1996).
Kozono et al., Production of soluble MHC class II proteins with covalently bound single peptides, Nature, 369:151-154 (1994).
Krogsgaard et al., "Visualization of Myelin Basic Protein (MBP) T Cell Epitopes in Multiple Sclerosis Lesions using a Monoclonal Antibody Specific for the Human Histocompatibility Leukokyte Antigen (HLA)-DR2-MBP 85-99 Complex," J. Exp. Med. 191(8):1395-1412, (Apr. 2000).
Kwok et al., "HLA-DQ Tetramers Identify Epitope-Specific T Cells in Peripheral Blood of Herpes Simplex Virus Type 2-Infected Individuals: Direct Detection of Immunodominant Antigen-Responsive Cells[1]," J. Immuno., 164:4244-4249 (2000).
Lanzavecchia et al., "Irreversible association of peptides with class II MHC molecules in living cells," Nature, 357:249-252 (1992).
Lee et al., "Structure of a human insulin peptide-HLA-DQ8 complex and susceptibility to type I diabetes," Nat. Immunol., 2:501-507 (2001).
Malcherek et al., "Supermotifs Enable Natural Invariant Chain-derived Peptides to Interact with Many Major Histocompatibility Complex-Class II Molecules," J. Exp. Med., 181:527-536 (1995).
Matsui et al., "Kinetics of T-cell receptor binding to peptide/I-E$^k$ complexes: Correlation of the dissociation rate with T-cell responsiveness," Proc. Natl. Acad. Sci., USA, 91:12862-12866 (1994).
Meyer et al., "Direct enumeration of Borrelia-reactive CD4 T Cells ex vivo by using MHC class II tetramers," Proc. Natl. Acad. Sci., USA, 97:11433-11438 (2000).

(Continued)

*Primary Examiner* — Gerald R Ewoldt
*Assistant Examiner* — Marianne DiBrino
(74) *Attorney, Agent, or Firm* — Foley Hoag LLP

(57) ABSTRACT

The present invention relates to novel compositions and methods for the generation of MHC class II compounds. Such methods are useful in identifying antigen-specific T cells, regulating an immune response and treating subjects suffering from an immune disorder.

6 Claims, 14 Drawing Sheets

OTHER PUBLICATIONS

Murali-Krishna et al., "Counting Antigen-Specific CD8 T Cells: A Reevaluation of Bystander Activation during Viral Infection," Immunity, 8:177-187 (1998).

Novak et al., "MHC class II tetramers identify peptide-specific human CD4+ T cells proliferating in response to influenza A antigen," J. Clin. Invest., 104:R63-67 (1999).

Riberdy et al., "HLA-DR molecules from an antigen-processing mutant cell line are associated with invariant chain peptides," Nature, 360:474-477 (1992).

Rosenberg et al., "Vigorous HIV-1-Specific CD4+ T Cell Responses Associated with Control of Viremia," Science, 278:1447-1450 (1997).

Savage et al., "A Kinetic Basis for T Cell Receptor Repertoire Selection during an Immune Response," Immunity, 10:485-492 (1999).

Scott et al., "Role of Chain Pairing for the Production of Functional Soluble IA Major Histocompatibility Complex Class II Molecules," J. Exp. Med., 183:2087-2095 (1996).

Stern, L.J. and Wiley, D.C., "The Human Class II MHC Protein HLA-DR1 Assembles as Empty $\alpha\beta$ Heterodimers in the Absence of Antigenic Peptide," Cell, 68:465-477(1992).

Valli et al., "Binding of Myelin Basic Protein Peptides to Human Histocompatibility Leukocyte Antigen Class II Molecules and Their Recognition by T Cells from Multiple Sclerosis Patients," J. Clin. Invest., 91:616-628 (1993).

Vonderheide et al., "Equivalent Induction of Telomerase-specific Cytotoxic T Lymphocytes from Tumor-bearing Patients and Healthy Individuals," Cancer Res., 61:8366-8370 (2001).

Wucherpfennig et al., "Structural Requirements for Binding of an Immunodominant Myelin Basic Protein Peptide to DR2 Isotypes and for Its Recognition by Human T Cell Clones," J. Exp. Med., 179:279-290 (1994).

Yu et al., "Binding of conserved islet peptides by human and murine MHC class II molecules associated with susceptibility to type I diabetes," Eur. J. Immunol., 30:2497-2506 (2000).

Zarutskie et al., "The kinetic basis of peptide exchange catalysis by HLA-DM," PNAS, 98(22):12450-12455 (Oct. 2001).

Altman et al., "Phenotypic Analysis of Antigen-Specific T Lymphocytes," Science, 274(5284):94-96 (1996).

Bikoff et al., "Distinct Peptide Loading Pathways for MHC Class II Molecules Associated with Alternative Ii Chain Isoforms," Journal of Immunology, 160(7):3101-3110 (1998).

Busch et al., "Accessory molecules for MHC class II peptide loading," Current Opinion in Immunology, 160(7):3101-3110 (1998).

Busch et al., "Stabilization of soluble, low-affinity HLA-DM/HLA-DR1 complexes by leucine zippers," Journal of Immunological Methods, 263(1-2):111-121 (2002).

Cunliffe et al., "Optimization of peptide linker length in production of MHC class II/peptide tetrameric complexes increases yield and stability, and allows identification of antigen-specific CD4+ T cells in peripheral blood mononuclear cells," European Journal of Immunology, 32(12):3366-3375 (2002).

Day et al., "Ex vivo analysis of human memory CD4 T cells specific for hepatitis C virus using MHC class II tetramers," The Journal of Clinical Investigation, 112(6):831-842 (2003).

Gauthier et al., "Expression and crystallization of the complex of HLA-DR2 (DRA, DRB1*1501) and an immunodominant peptide of human myelin basic protein," Proceedings of the National Academy of Sciences USA, 95(1):11828-11833 (1998).

Jensen et al., "Peptide exchange in MHC molecules," Immunological Reviews, 172:229-238 (1999).

Kropshofer et al., "Structural features of the invariant chain fragment CLIP controlling rapid release from HLA-DR molecules and inhibition of peptide binding," Proceedings of the National Academy of Sciences USA, 92(18):8313-8317 (1995).

Meyer et al., "Direct enumeration of *Borrelia* -reactive CD4 T cells ex vivo by using MHC class II tetramers," Proceedings of the Academy of Sciences USA, 97(21):11433-11438 (2000).

Zhu et al., "A recombinant single-chain human class II MHC molecule (HLA-DR1) as a covalently linked heterotrimer of $\alpha$ chain, $\beta$ chain, and antigenic peptide, with immunogenicity in vitro and reduced affinity for bacterial superantigens," Eur. J. Immunol., 27(8):1933-1941 (1997).

Supplementary European Search Report from EP 03 75 5725 (DFS-044.80) dated Jan. 13, 2009.

* cited by examiner

A. Gel filtration chromatography

B. Affinity chromatography

C. Multimerization of HLA-DR4 with Strepavidin

HLA-DR4 and HIV p24 (166-179)

A.

B.

C.

A. Before enrichment for DRB1*0401 T tramer+ cells

B. After enrichment for DRB1*0401 Tetramer+ cells

C. Functionality of 98A HCV-stimulated line

A. Subject 01-40

B. HCV/HIV-seronegative DRB1*0401 control

C. Subject 99-24

A. 01-40 Fresh PBMC

B. 01-40 NS3/4-stimulated line

C. 98A NS3/4-stimulated line

COMPOSITIONS AND METHODS FOR THE GENERATION OF MHC CLASS II COMPOUNDS BY PEPTIDE EXCHANGE

RELATED APPLICATIONS

This application claims the benefit of U.S. Provisional Application Ser. No. 60/395,494, filed on Jul. 12, 2002 and U.S. Provisional Application Ser. No. 60/397,893, filed on Jul. 22, 2002, the entire contents of which are incorporated herein by reference.

BACKGROUND AND SIGNIFICANCE

The initiation of an immune response against a specific antigen in mammals is brought about by the presentation of that antigen to T lymphocytes. An antigen is presented to T lymphocytes in the context of a major histocompatability (MHC) complex (also referred to as HLA in humans and H-2 in mice). The three-dimensional structure of the MHC includes a groove or cleft into which the presented antigen fits. When an appropriate receptor on a T lymphocyte (also known as the T cell receptor, or TCR) interacts with the MHC/antigen complex on an antigen-presenting cells (APC) in the presence of necessary co-stimulatory signals, the T lymphocyte is stimulated, triggering various aspects of the well characterized cascade of immune system activation events, including induction of cytotoxic T lymphocyte (CTL) function, induction of B lymphocyte function and stimulation of cytokine production (see, e.g. Roitt, I and Delves, P. *Roitt's Essential Immunology*, 10$^{th}$ Ed., Boston, Blackwell Science, 2002; Abbas, A. et al. *Cellular and Molecular Immunology*, W.B. Saunders Company, Philadelphia, 1991; Silverstein, A. *A History of Immunology*, San Diego, Academic Press, 1989).

MHC/peptide complexes have a low affinity for the TCR, and dissociate rapidly with a $t_{1/2}$ of approximately 2 to 12 seconds (measured at 25° C.) (see, e.g., Matsui, K. et al. (1994) *Proc. Natl. Acad. Sci., USA* 91:12862). Multimerization on a steptavidin scaffold permits multivalent binding to the TCR and slow dissociation of tetramers from T cells with the appropriate MHC/peptide specificity (i.e., $t_{1/2}$ of 20 to 240 minutes for tetramer dissociation from murine cytochrome C specific T cells) (see, e.g., Savage, P. A. et al. (1999) *Immunity* 10:485). The ability to directly visualize antigen specific CD8$^+$ T cells has led to a reappraisal of the magnitude of virus specific T cell responses in acute and chronic infections since the frequency of such T cells had been greatly underestimated by limiting dilution analyses (Murali-Krishna, K. et al. (1998) *Immunity* 8:177). Tetramers for MHC class I/peptide complexes have therefore become an indispensable tool for both basic and clinical scientists in the investigation of anti-viral T cell responses. The success of tetramers of MHC class I/peptide complexes is largely due to the fact that the MHC class I heavy chain and β$_2$-microglobulin can be reliably refolded from subunits expressed in *E. coli* in the presence of appropriate peptides (see, e.g., Garboczi, D. N. et al. (1992) *Proc. Natl. Acad. Sci., USA* 89:3429 and Altman, J. D. et al. (1996) *Science* 274:94).

By comparison, development of MHC class II tetramers has been far more challenging. Thus far, antigen-specific human CD4$^+$ T cells have only been detected with MHC class II tetramers in a single human disease, chronic Lyme arthritis, where T cells against a previously defined peptide from the OspA antigen were visualized in the synovial fluid from two of three patients with the disease (Meyer, A. L. et al. (2000) *Proc. Natl. Acad. Sci., USA* 97:11433). The difficulty in the application of MHC class II tetramers to the investigation of human diseases relates, at least in part, to the greater difficulty of expressing functional molecules. The majority of human and murine MHC class II molecules have not been successfully refolded from α and β chains produced in *E. coli*, which has necessitated the development of alternative approaches (see, e.g., Frayser, M. et al. (1999) *Protein Expr. Purif.* 15:105). Expression of the MHC α and β ectodomains in eukaryotic cells results in the secretion of "empty" molecules, and a fraction of these molecules can be loaded with peptides (see, e.g., Stern L. J. and Wiley, D. C. (1992) *Cell* 68:465). Depending on the isotype and allele, such "empty" molecules have a tendency to aggregate and a substantial fraction of these molecules can be inactive. Tetramers have been made using this approach and have been shown to stain T cell lines grown in vitro with viral antigen-peptide in the presence of recombinant interleukin (IL)-2, but have not yet been used to directly identify virus-specific T cell populations from peripheral blood without prior in vitro expansion of T cells (see, e.g., Novak, E. J. et al. (1999) *J. Clin. Invest.* 104:R63 and Kwok, W. W. et al. (2000) *J. Immunol.* 164:4244). Reasons for these shortcomings include very low frequency of virus specific T cells and/or insufficient binding of tetramers to relevant T cell populations.

Due to the long half-life of bound peptides, the kinetics of peptide binding to HLA-DR molecules purified from antigen presenting cells is very slow. Even with extended incubation times, only a small fraction of MHC class II molecules can be loaded with defined peptides since high affinity peptides have exceptionally long half-lives (see, e.g., Lanzavecchia, A. et al. (1992) *Nature* 357:249 and Jensen, P. E. et al. (1992) *J. Exp. Med.* 176:793). The kinetics of peptide association are also relatively slow for empty DR1 molecules refolded from subunits expressed in *E. coli* in the absence of any peptide. Biphasic kinetics were observed with τ=4 hours for the initial faster phase and τ=24 hours for the second slower phase, and even after an extended incubation (4 days) only a fraction of molecules were loaded with the high affinity influenza HA peptide. The slow kinetics are due to the fact that only a small fraction of empty DR1 molecules (1-5%) are in a peptide-receptive form, and that the overall reaction rate is determined by the slow conversion from the peptide-averse form (Zarutskie, J. A. et al. (1998) *J. Exp. Med.* 188:2205).

To solve this problem, MHC class II tetramers have been generated by covalently linking the peptide of interest to the N-terminus of the MHC class II β chain (see, e.g., Kappler, J. W. and Marrack, P., U.S. Pat. No. 5,820,866; Crawford, F. et al. (1998) *Immunity* 8:675; and Kozono, H. et al. (1994) *Nature* 369:151). While this approach is particularly suitable when a single tetramer is required (i.e., such as for tracking T cells from TCR transgenic mice), it is not suited to a clinical setting where the relevant T cell epitopes are not yet known with certainty because of the need to create a new transfectant/recombinant virus for each peptide of interest. In addition, due to the variable contributions of a number of peptide residues (at least 4 or 5) involved in MHC class II binding, epitope prediction methods for MHC class II molecules are not as reliable as those widely used for MHC class I molecules, even though these prediction methods are based on detailed biochemical studies with several MHC class II molecules (see, e.g., Hammer, J. et al. (1993) *Cell* 74:197). As such, successful application of MHC class II compounds, such as MHC class II tetramers, to a clinical setting would require an approach that permits the generation of sets of compounds with biochemically well-defined MHC class II/peptide complexes, preferably such that many different peptides can be evaluated without prior knowledge of relevant CD4$^+$ T cell epitopes.

SUMMARY OF THE INVENTION

The present invention provides novel compositions and methods for the generation of MHC class II compounds. Advantages of the methods of the present invention include (1) a single, well-defined protein preparation can be used for the generation of multiple compounds, e.g., monomers and multimers, such as dimers, trimers and tetramers, as well as higher-order multimers; (2) several antigen-specific MHC class II compounds can be produced without knowing the specific epitope; and (3) the necessary processing steps, i.e. processing of the first linker and activating the effector molecule, can be performed in a single tube before the protein is divided into multiple peptide exchange reactions.

In one embodiment, an MHC class II compound is provided that includes: an MHC class II component which comprises (1) at least a portion of an MHC class II α chain and at least a portion of an MHC class II β chain, such that the MHC class II α and β chains from a peptide binding groove; (2) a spaceholder molecule, wherein the spaceholder molecule binds within the peptide binding groove thereby hindering the binding of any other peptide within the peptide binding groove; and (3) an effector component, wherein the effector component is linked to the MHC class II component.

In one embodiment, the spaceholder molecule is covalently bound to the peptide groove. In another embodiment, the spaceholder molecule binds to the peptide binding groove with intermediate affinity. In a further embodiment, the spaceholder molecule binds to the peptide binding groove with low affinity. As used herein, a "spaceholder molecule" is a peptide that occupies the peptide binding site during biosynthesis and purification, thereby preventing the binding of irrelevant peptides as well as aggregation of the MHC protein. Such spaceholder molecules may have a low to intermediate affinity for the MHC protein thereby enabling the exchange of a peptide of interest in a peptide exchange reaction following cleavage of the processable linker. Examples of spaceholder molecules include, but are not limited to, PVSKMRMAT-PLLMQA (SEQ ID NO:1); AAMAAAAAAAMAA (SEQ ID NO:2); AAMAAAAAAAMAA (SEQ ID NO:3); AAFAAAAAAAAAA (SEQ ID NO:4); and ASM-SAASAASMAA (SEQ ID NO:5). In one embodiment, the spaceholder molecule will have the consensus sequence AAXAAAAAAAXAA (SEQ ID NO:36), wherein X is any amino acid.

In a further embodiment, the spaceholder molecule is covalently linked to the MHC component. In yet another embodiment, the effector component is covalently linked to the MHC component.

In another embodiment, the effector component is a label, e.g. without limitation, a fluorescent label, biotin, at least a portion of an immunoglobulin protein, a metallic compound, luciferin, a radiolabel and an enzyme.

In another embodiment, an MHC class II compound is provided that includes (1) an MHC class II component that comprises at least a portion of an MHC class II α chain and at least a portion of an MHC class II β chain, such that the MHC class II α and β chains form a peptide binding groove; (2) an antigenic peptide molecule, wherein the antigenic peptide molecule binds within the peptide binding groove; and (3) an effector component which is linked to the MHC class II component. In a further embodiment, the effector component is a label, e.g., without limitation, a fluorescent label, biotin, at least a portion of an immunoglobulin protein, a metallic compound, luciferin, a radiolabel, a cytokine, a viral capsid protein and an enzyme.

In another embodiment, the antigenic peptide molecule comprises an affinity tag e.g., dinitrophenol (DNP), and an antigen peptide, such as a portion of an autoantigen, an infectious antigen, a toxin, an allergen and a tumor-associated antigen. In certain embodiments, the affinity tag is covalently linked to the antigen peptide.

In yet another embodiment, the MHC class II compound is encoded by a nucleic acid molecule. In certain embodiments, the nucleic acid molecule comprises a nucleic acid sequence encoding a signal segment attached to the N-terminus of the MHC class II compound. These nucleic acid molecules can further be operatively linked to an expression vector to form a recombinant molecule. These recombinant molecules can further be transformed into a host cell, e.g., a bacterial, fungal, insect or mammalian cell, to produce a recombinant cell which expresses the recombinant molecule.

Another aspect of the invention provides for a method of producing an MHC class II compound. The methods of the present invention comprise the steps of (1) culturing a cell transformed with at least one nucleic acid molecule comprising (a) an MHC class II component, wherein the MHC class II component comprises at least a portion of an MHC class II α chain and at least a portion of an MHC class II β chain, such that the MHC class II α chain and MHC class II β chain form a peptide binding groove; (b) a spaceholder molecule which binds to the MHC class II compound by a processable linker, whereby the spaceholder molecule binds within the peptide binding groove and prevents the binding of any other peptide within the peptide binding groove of the MHC class II compound; and (c) an effector component which is linked to the MHC class II component by a second linker; (2) recovering the MHC class II compound; (3) processing the processable linker thereby releasing the spaceholder molecule from the peptide binding groove; (4) incubating the MHC class II compound in the presence of an antigenic peptide molecule whereby the incubation facilitates the binding of the antigen peptide molecule to the peptide binding groove of the MHC class II compound; and (5) recovering the MHC class II compound that has bound the antigenic peptide.

In another embodiment, the step of incubating the MHC class II compound with the antigenic peptide molecule is repeated with different antigenic peptides in order to produce several MHC class II compounds that recognize several antigenic epitopes. In another embodiment, the incubating step is performed in vitro.

Another aspect of the invention provides methods for identifying an antigen-specific MHC class II bearing T cell from a subject, e.g., a mammal, such as a human, comprising the steps of culturing an MHC class II compound produced according to the methods of the present invention with at least one isolated T cell to form an MHC class II compound-T cell complex. This complex is then isolated and assayed to identify the T cell which bound the MHC class II compound. In certain embodiments, the identification is performed ex vivo. In certain embodiments, the subject is suffering from an immune disorder, e.g., a subject infected with a virus, bacteria, parasite, a neoplastic disease or a toxin. The compositions and methods may therefore be used to isolate and characterize T cells which recognize antigens associated with the immune disorder, to identify the specific antigen which will modulate the most beneficial immune response, and to treat a subject suffering from an immune disorder, e.g., utilizing the newly identified antigen to create an antibody for administration to the subject.

Another aspect of the invention pertains to methods of regulating an immune response comprising the steps of administering to a subject an effective amount of an isolated MHC class II compound produced according to the methods of the present invention, such that the immune response in the subject is regulated. The invention also provides a method of treating an immune disorder in a subject comprising administering to a subject an effective amount of an isolated MHC class II compound according to the methods of the present invention, such that the immune disorder is treated.

Another aspect of the invention pertains to methods of regulating an immune response ex vivo comprising the steps of isolating a T cell population from a subject, contacting the T cell population with an effective amount of an isolated MHC class II compound of the present invention, and re-administering the T cell population back into the subject, thereby regulating the immune response.

Yet another aspect of the invention provides a method of treating an immune disorder in a subject ex vivo comprising the steps of isolating a T cell population from a subject, contacting the T cell population with an effective amount of an isolated MHC class II compound of the present invention, and readministering the T cell population back into the subject, thereby treating the immune disorder in the subject.

The present invention is also directed to pharmaceutical compositions comprising an MHC class II compound of the present invention and a pharmaceutically acceptable carrier.

BRIEF DESCRIPTION OF THE DRAWINGS

FIG. 2A shows the HLA-DR peak observed during gel filtration chromatography. FIG. 2B shows the affinity purification of HLA-DR molecules loaded with defined peptides. FIG. 2C shows the multimerization of biotinylated HLA-DR with streptavidin as observed by gel electrophoresis.

DETAILED DESCRIPTION OF THE INVENTION

Figure 1:
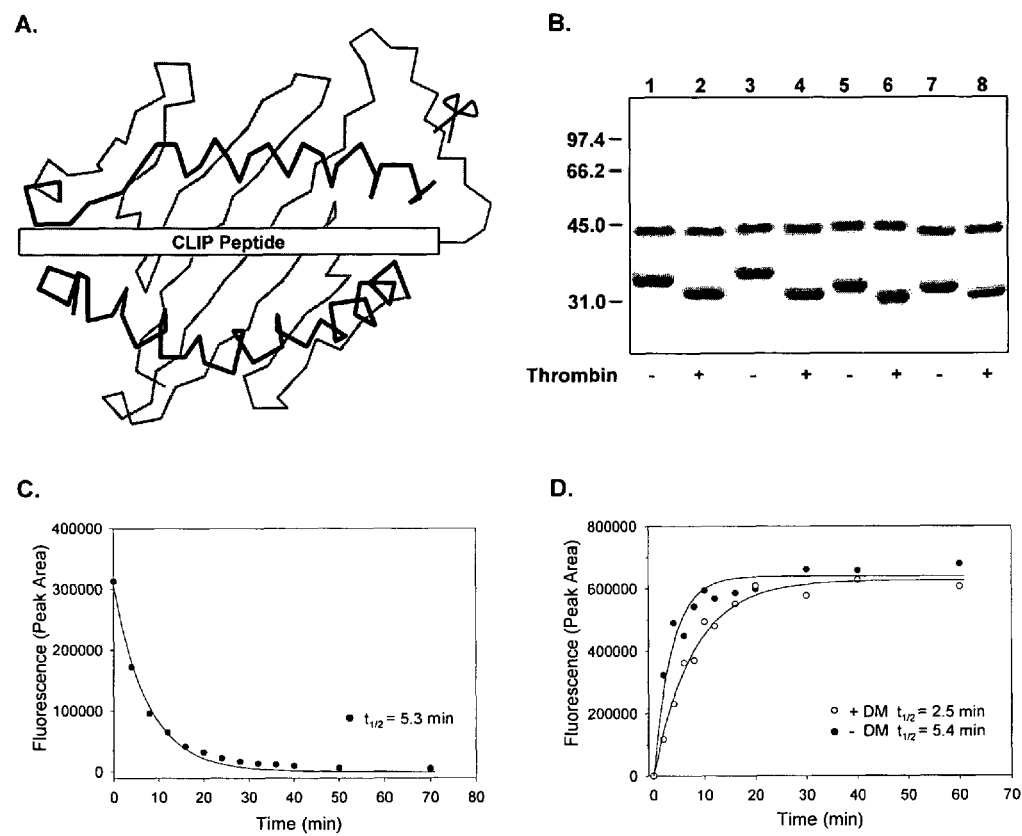
FIG. 1A is a schematic representation of the spaceholder CLIP peptide that is covalently attached to the MHC molecule through a linker with a protease cleavage site.
FIG. 1B illustrates a SDS-PAGE assay showing the molecular weight change of HLA-DR/CLIP complexes after cleavage by thrombin.
FIGS. 1C and 1D illustrate the kinetic properties of CLIP dissociation from the HLA-DR molecule and peptide association with the HLA-DR molecule, respectively.

The present invention relates, at least in part, to novel compositions and methods for producing MHC class II compounds. In one embodiment, an MHC class II compound is provided that includes (1) an MHC class II component which comprises at least a portion of an MHC class II α chain and at least a portion of an MHC class II β chain, such that the MHC class II α and β chains from a peptide binding groove; (2) a spaceholder molecule, wherein the spaceholder molecule binds within the peptide binding groove thereby hindering the binding of any other peptide within the peptide binding groove; and (3) an effector component, wherein the effector component is linked to the MHC class II component.

In another embodiment, an MHC class II compound is provided that includes (1) an MHC class II component that comprises at least a portion of an MHC class II α chain and at least a portion of an MHC class II β chain, such that the MHC class II α and β chains form a peptide binding groove; (2) an antigenic peptide molecule, wherein the antigenic peptide molecule binds within the peptide binding groove; and (3) an effector component which is linked to the MHC class II component. In a further embodiment, the effector component is a label, e.g. without limitation, a fluorescent label, biotin, at least a portion of an immunoglobulin protein, a metallic compound, luciferin, a radiolabel and an enzyme.

Another aspect of the invention provides for a method of producing an MHC class II compound. The methods of the present invention comprise the steps of (1) culturing a cell transformed with at least one nucleic acid molecule comprising an MHC class II component, wherein the MHC class II component comprises (a) at least a portion of an MHC class II α chain and at least a portion of an MHC class II β chain, such that the MHC class II α chain and MHC class II β chain form a peptide binding groove; (b) a spaceholder molecule which binds to the MHC class II compound by a processable linker, whereby the spaceholder molecule binds within the peptide binding groove and prevents the binding of any other peptide within the peptide binding groove of the MHC class II compound; and (c) an effector component which is linked to the MHC class II component by a second linker; (2) recovering the MHC class II compound; (3) processing the processable linker thereby releasing the spaceholder molecule from the peptide binding groove; (4) incubating the MHC class II compound in the presence of an antigenic peptide molecule whereby the incubation facilitates the binding of the antigen peptide molecule to the peptide binding groove of the MHC class II compound; and (5) recovering the MHC class II compound that has bound the antigenic peptide.

In another embodiment, the step of incubating the MHC class II compound with the antigenic peptide molecule is repeated with different antigenic peptides in order to produce several MHC class II compounds that recognize several antigenic epitopes. In another embodiment, the incubating step is performed in vitro.

Another aspect of the invention provides methods for identifying an antigen-specific MHC class II bearing T cell from a subject, e.g., a mammal, such as a human, comprising the steps of culturing an MHC class II compound produced according to the methods of the present invention with at least one isolated T cell to form an MHC class II compound-T cell complex. This complex is then isolated and assayed to identify the T cell which bound the MHC class II compound. In certain embodiments, the identification is performed ex vivo. In certain embodiments, the subject is suffering from an immune disorder, e.g., a subject infected with a virus, bacteria, parasite, a neoplastic disease or a toxin. The compositions and methods may therefore be used to isolate and characterize T cells which recognize antigens associated with the immune disorder, to identify the specific antigen which will modulate the most beneficial immune response, and to treat a subject suffering from an immune disorder, e.g. utilizing the newly identified antigen to create an antibody for administration to the subject.

Another aspect of the invention pertains to methods of regulating an immune response comprising the steps of administering to a subject an effective amount of an isolated MHC class II compound of the present invention, such that the immune response in the subject is regulated. The invention also provides a method of treating an immune disorder in a subject comprising administering to a subject an effective amount of an isolated MHC class II compound of the present invention, such that the immune disorder is treated.

Another aspect of the invention pertains to methods of regulating an immune response ex vivo comprising the steps of isolating a T cell population from a subject, contacting the T cell population with an effective amount of an isolated MHC class II compound of the present invention, and re-administering the T cell population back into the subject, thereby regulating the immune response.

Yet another aspect of the invention provides a method of treating an immune disorder in a subject ex vivo comprising the steps of isolating a T cell population from a subject, contacting the T cell population with an effective amount of an isolated MHC class II compound of the present invention, and readministering the T cell population back into the subject, thereby treating the immune disorder in the subject.

The present invention is also directed to pharmaceutical compositions comprising an MHC class II compound of the present invention and a pharmaceutically acceptable carrier.

The major histocompatability complex (MHC) is a collection of genes encoding glycoproteins called MHC proteins. The primary function of an MHC protein in vivo is to present antigen in a form capable of being recognized by a TCR. An MHC protein is bound to an antigen in the form of an antigenic peptide to form an MHC-peptide complex.

As used herein, "TCR recognition" refers to the ability of a TCR to bind to an MHC peptide complex. The presentation of antigen by an MHC protein to the T cell normally leads to a T cell response that is clone specific. Normal T cells are distinguished from T cell hybridomas which may differ from normal T cells in their activation reactions. As used herein, "antigen presentation" refers to presenting antigen in such a manner that at least a portion of the antigen is available to be bound by a TCR. A T cell response occurs when a TCR recognizes an MHC protein bound to an antigenic peptide, thereby altering the activity of the T cell bearing the TCR. As used herein, a "T cell response" can refer to the activation, induction of anergy, or death of a T cell that occurs when the TCR of the T cell is bound by an MHC-peptide complex. As used herein, "activation" of a T cell refers to induction of signal transduction pathways in the T cell resulting in production of cellular products (e.g., interleukin-2) by that T cell. "Anergy" refers to the diminished reactivity by a T cell to an antigen. Activation and anergy can be measured by, for example, measuring the amount of IL-2 produced by a T cell after an MHC-peptide complex has bound to the cell's TCR. Anergic cells will have decreased IL-2 production when compared with stimulated T cells. Another method for measuring the diminished activity of anergic T cells includes measuring intracellular calcium mobilization by a T cell upon engagement of its TCRs. As used herein, "T cell death" refers to the permanent cessation of substantially all functions of the T cell and is used interchangeably with the art known terms "apoptosis" and "programmed cell death (PCD)."

MHC proteins, also known as human leukocyte antigen (HLA) in humans and H-2 region in mice, are classified in two categories: class I and class II MHC proteins. These proteins are comprised of a cluster of highly polymorphic genes. Specifically, human HLA-A, HLA-B, and HLA-C are known as class I MHC molecules, whereas human HLA-DP, HLA-DQ and HLA-DR are known as class II MHC molecules. The HLA loci include HLA-DP, HLA-DN, HLA-DM, HLA-DO, HLA-DQ, HLA-DR, HLA-A, HLA-B and HLA-C. The MHC class II component of the present invention may comprise any of these different MHC class II loci. Furthermore, each of these loci contains different alleles in the human population. The different subtypes encoded by these allelic variants are also intended to be within the scope of the invention.

An MHC class II protein is a heterodimeric integral membrane protein comprising one α and one β chain in noncovalent association. The α chain has two extracellular domains ($\alpha_1$ and $\alpha_2$), and a transmembrane (TM) and a cytoplasmic (CYT) domain. The β chain contains two extracellular domains ($\beta_1$ and $\beta_2$), and a TM and CYT domain. An MHC class I protein is an integral membrane protein comprising a glycoprotein heavy chain having three extracellular domains (i.e., $\alpha_1$, $\alpha_2$ and $\alpha_3$), and a TM and CYT domain. The heavy chain is noncovalently associated with a soluble subunit called $\beta_2$-microglobulin ($\beta_{2m}$).

Antigenic peptides associate with an MHC protein by binding to a peptide binding site of an MHC protein. As used herein, the term "peptide binding site" or "peptide binding groove" refers to the portion of an MHC protein capable of binding peptide. The conformation of a peptide binding site is capable of being altered upon binding of an antigenic peptide to enable proper alignment of amino acid residues important for TCR binding to the MHC protein and or peptide.

The domain organization of class II proteins form the peptide binding site. A binding groove of an MHC class II compound can comprise portions of the $\alpha_1$ and $\beta_1$ domains capable of forming two β-pleated sheets and two α helices. Without being bound by theory, it is believed that a first portion of the $\alpha_1$ domain forms a first β-pleated sheet and a second portion of the $\alpha_1$ domain forms a first α helix. A first portion of the $\beta_1$ domain forms a second β-pleated sheet and a second portion of the $\beta_1$ domain forms a second α helix. The x-ray crystallographic structure of class II protein with a peptide engaged in the binding groove of the protein indicates that one or both ends of the engaged peptide can project beyond the MHC protein (Brown et al. (1993) *Nature* 364: 33). Thus, the ends of the $\alpha_1$ and $\beta_1$ α helices of class II apparently form an open cavity such that the ends of the peptide bound to the binding groove are not buried in the cavity. Moreover, the x-ray crystallographic structure of class II proteins indicates that the N-terminal end of the MHC β chain apparently projects from the side of the MHC protein in an unstructured manner since the first 4 amino acid residues of the β chain could not be assigned by x-ray crystallography.

According to the present invention, "at least a portion of" refers to a portion of an MHC protein capable of forming a peptide binding site or capable of forming a binding site upon addition of another chain of an MHC protein. Preferred MHC molecules of the present invention include segments having at least a portion of a class II MHC protein.

As used herein, the term "MHC class II compound" includes monomers and multimers, such as dimers, trimers and tetramers as well as higher-order multimers. In one embodiment, an MHC class II compound of the present invention can include at least a portion of a single chain such as a class II α chain or a class II β chain. MHC class II compound containing such MHC molecules can be combined with an appropriate distinct MHC protein chain capable of associating with the MHC class II compound to form a complex having a functional peptide binding site. A preferred class II α chain of the present invention contains class II $\alpha_1$ and $\alpha_2$ domains. A preferred class II β chain contains $\beta_1$ and $\beta_2$ domains. Preferred embodiments of an MHC class II compound of the present invention include molecules having a class II β chain which includes a $\beta_1$ domain, a $\beta_2$ domain, and a molecule having a class II β chain which includes a $\beta_1$ domain, a β chain transmembrane domain and a β chain cytoplasmic domain.

An antigenic peptide molecule of the present invention may comprise any peptide that is capable of binding to an MHC protein in a manner such that the MHC-peptide complex can bind to TCR and affect a T cell response. A peptide of the present invention can be synthesized by a cell, externally or internally hydrolyzed, or a post-translation modification product as well as synthesized in vitro using techniques known in the art. For example, the characteristics of the antigenic peptides, such as the length, amino acid composition, and the like will depend on several factors, including, but not limited to, the ability of the peptide to fit within the peptide binding groove, experimental conditions and the antigen of interest to the investigator. These factors can be determined by one skilled in the art without undue experimentation through the use of commercially available computer programs, such as Protean II™ (Proteus) and SPOT™. This allows for several possible antigenic epitopes to be generated for use in the present invention, therefore eliminating the cumbersome and expensive step of epitope identification.

Antigenic peptides that are produced by hydrolysis of antigens undergo hydrolysis prior to binding of the antigen to an MHC protein. For example, class II MHC proteins typically present antigenic peptides derived from exogenous protein that enter a cell's endocytic pathway. Intracellular trafficking permits an antigenic peptide to become associated with an MHC protein. The resulting MHC-peptide complex then travels to the surface of the cell where it is available for interaction with a TCR.

Suitable antigenic peptides of the present invention include peptides comprising at least a portion of an antigen selected from a group consisting of autoantigens, tumor associated antigens (TAA), infectious agents, toxins, allergens, or mixtures thereof. Preferred TAA of the present invention are associated with tumor cells that have arisen spontaneously, e.g. in a human subject, or may be experimentally derived or induced, e.g. in an animal subject. The tumor cells can be obtained, for example, from a solid tumor of an organ, such as a tumor of the lung, liver, breast, colon, bone etc. Malignancies of solid organs include, but are not limited to, carcinomas, sarcomas, melanomas and neuroblastomas. The tumor cells can also be obtained from a blood-borne (i.e. dispersed) malignancy such as a lymphoma, a myeloma or a leukemia. As used herein, a "tumor" includes a normal benign or malignant mass of tissue. Preferred autoantigens of the present invention include, but are not limited to, antigens which result in the development of insulin dependent diabetes mellitus, arthritis (including rheumatoid arthritis, juvenile arthritis, and psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, iritis, conjunctivitis, keratoconjunctivitis, ulcerative colitis, asthma, allergic asthma, cutaneous lupus erythematosus, scleroderma, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, and interstitial lung fibrosis. Examples of infectious agents of the present invention include, but are not limited to, bacteria, viruses, and eukaryotic parasites. Preferred animal parasites include protozoan parasites, helminth parasites (such as nematodes, cestodes, trematodes, ectoparasites and fungi). Examples of allergens of the present invention include, but are not limited to plant, animal, bacterial, parasitic allergens and metal-based allergens that cause contact sensitivity. Allergens include, for example, weed, grass, tree, peanut, mite, flea, and cat antigens. Examples of toxins of the present invention include, but are not limited to, staphylococcal enterotoxins, toxic shock syndrome toxin, retroviral antigens, streptococcal antigens, mycoplasma, mycobacterium, and herpes viruses. Retroviral antigens include antigens derived from human immunodeficiency virus. Toxins include SEA, SEB, $SE_{1-3}$, SED, and SEE.

An antigen peptide molecule of the present invention contains a novel linker which comprises an amino acid sequence that covalently associates an affinity tag with an antigenic peptide. Covalent bonds are formed between the antigenic peptide and the linker, and between the linker and the affinity tag. The antigen peptide may be covalently linked to the affinity tag by a linker having the length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acid residues in length.

The affinity tag of the present invention may be any substrate, compound or analog thereof which is capable of binding naturally to the active site(s) of proteins, enzymes, antibodies, steroids, or physiological receptors. An affinity tag may also be any hapten to which an antibody, i.e. a monoclonal or polyclonal, can be raised against. These tags are useful in affinity purification, e.g., affinity chromatography, a technique well-known to those skilled in the art and described in further detail in the Examples section. In certain embodiments, an affinity tag may be dinitrophenol (DNP).

In a further embodiment, an MHC class II compound of the present invention can include an effector component. The effector component can be conjugated to the α or β chain of the MHC molecule. Examples of suitable effector molecules include those which permit the generation of multimers (e.g., immunoglobulin domains, viral capsid proteins, chemical groups that permit binding to a multimeric protein or chemical scaffold), cytokines which modulate the response of the T cells to which the MHC class II compound is bound, a label or a toxin. Suitable toxins include, but are not limited to, double chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, alpha-amanitin, and ribosome inhibiting proteins; and chemical toxins, such as melphalan, methotrexate, nitrogen mustard, doxorubicin and daunomycin. Suitable labels include, but are not limited to, a fluorescent label, biotin, at least a portion of an immunoglobulin protein, metallic compounds, luciferin, radiolabels and enzymes.

In certain embodiments, the present invention provides for the visualization of antigen-specific T cells. The addition of the affinity tag component and effector component allows for one skilled in the art to (1) isolate and purify the antigen-specific r cell which binds to the MHC class II compound using techniques commonly used by those skilled in the art (i.e., affinity chromatography) and (2) visualize this population of MHC class II compounds by activating the effector component of the MHC class II compound. For example, if biotin is used as the effector component, isolated MHC class II compounds can be visualized with labeled streptavidin. A more detailed procedure for the visualization of MHC class II compounds of the present invention is provided in the Examples section below.

The compositions and methods of the present invention employ the use of a spaceholder molecule linked to the MHC class II compound, e.g., the β chain, by a processable linker. A spaceholder molecule of the present invention may be any peptide that is capable of binding to a peptide binding groove of an MHC protein in such a manner that binding of any other peptide in the peptide binding groove is hindered. Preferably, the spaceholder molecule binds within the peptide binding groove with intermediate affinity, and more preferably with low affinity, at approximately neutral pH. In one embodiment, the length of a spaceholder molecule extends from about 5 to about 40 amino acid residues, more preferably from about 6 to about 30 amino acid residues, 8 to about 20 amino acid residues and even more preferably from about 12 to 15 amino acids residues. In a further embodiment, a spaceholder molecule is about 13 amino acids residues. Examples of suitable spaceholder molecules include, without limitation, (in single letter amino acid code) PVSKMRMATPLLMQA (SEQ ID NO:1), also known as CLIP; AAMAAAAAAAMAA (SEQ ID NO:2); AAMAAAAAAAAAA (SEQ ID NO:3); AAFAAAAAAAAAA (SEQ ID NO:4); ASMSAASAAS-MAA (SEQ ID NO:5), and functional equivalents thereof. In one embodiment, the spaceholder molecule will have the consensus sequence AAXAAAAAAAXAA (SEQ ID NO:36), wherein X is any amino acid. The ability of maintaining a spaceholder molecule within the binding groove of the MHC class II molecule prevents "empty" molecules from forming. The formation of "empty" MHC class II molecules has been a major limiting factor due to the tendency of these "empty" molecules to aggregate, thus making isolation of functional MHC class II compounds difficult.

The spaceholder molecule of the present invention may be covalently linked to the MHC molecule by a linker having an amino acid sequence that contains a target site for an enzyme capable of cleaving proteins. Such linkers are referred to herein as "processable linkers". Examples of processable linkers of the present invention include linkers containing target sites for enzymes such as collagenases, metalloproteases, serine proteases, cysteine proteases, kallikriens, thrombin, and plasminogen activators. A preferred processable linker of the present invention includes a linker having a thrombin cleavage site.

Suitable linkers useful in the present invention can also be designed using various methods. For example, x-ray crystallographic data of an MHC protein can be used to design a linker of suitable length and charge such that the linker does not interfere with the binding of the spaceholder molecule to the peptide binding groove of the MHC class II compound. Such methods are included in the present invention.

The length of a linker of the present invention is preferably sufficiently short (i.e., small enough in size) such that the linker does not substantially inhibit binding between the spaceholder molecule and the MHC class II compound. The length of a linker of the present invention may range from about 1 amino acid residue to about 40 amino acid residues, more preferably from about 5 amino acid residues to about 30 amino acid residues, and even more preferably from about 8 amino acid residues to about 20 amino acid residues.

The cleavage of the linker facilitates the release of the spaceholder molecule thereby freeing the peptide binding groove. The MHC class II compound of the present invention may then be incubated with the antigen peptide molecule to facilitate the binding of the antigen peptide molecule to the MHC class II compound. After sufficient time to allow binding, which can be readily determined by one skilled in the art, the MHC class II compound which has bound to the antigen peptide molecule is recovered.

In certain embodiments, the step of cleaving the linker and incubating with the antigen peptide molecule is repeated using different antigen peptide molecules. The advantage of repeating these steps is to allow for the formation of a number of MHC class II compounds that recognize several antigenic epitopes. Furthermore, these steps can be carried out using MHC class II molecules constructed with varying allelic forms of the MHC class II genes. This feature of the present invention therefore allows for the generation of several MHC class II compounds which are specific for a number of different MHC allelic genotypes, thereby greatly increasing the number of individuals to which the present invention can be applied.

Another aspect of the present invention relates to a nucleic acid molecule that encodes a protein of the present invention comprising the MHC class II compounds disclosed herein. According to the present invention, references to nucleic acids also refer to nucleic acid molecules. A nucleic acid molecule can be DNA, RNA, or hybrids or derivatives of either DNA or RNA. Nucleic acid molecules of the present invention can include regulatory regions that control expression of the nucleic acid molecule (e.g., transcription or translation control regions), full-length or partial coding regions, and combinations thereof. Any portion of a nucleic acid molecule of the present invention can be produced by: (1) isolating the molecule from its natural milieu; (2) using recombinant DNA technology (e.g., PCR amplification, cloning); or (3) using chemical synthesis methods. A nucleic acid of the present invention can include functional equivalents of natural nucleic acid molecules encoding an MHC molecule or a peptide, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein of the present invention capable of forming compositions that can be recognized by T cell receptors. Preferred functional equivalents include sequences capable of hybridizing under stringent conditions, to at least a portion of an MHC class II compound encoding nucleic acid molecule (according to conditions described in Sambrook et al., Molecular Cloning: A Laboratory Manual, Cold Spring Harbor Labs Press, 1989, which is incorporated herein by reference in its entirety). As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a working peptide binding domain, a TCR binding domain and a linker that does not substantially interfere with desired binding interactions. Functional tests for these various characteristics (e.g., binding studies) allows one of skill in the art to determine what modifications to nucleic acid sequences would be appropriate and which would not.

One embodiment of the present invention includes a nucleic acid molecule encoding an MHC class II compound comprising an MHC class II component which includes at least a portion of an MHC class II α chain and at least a portion of an MHC class II β chain, such that said MHC class II α chain and β chains form a peptide binding groove; a spaceholder molecule; and an effector molecule. Another embodiment of the present invention includes a nucleic acid molecule encoding an MHC class II compound comprising an MHC class II component which includes at least a portion of an MHC class II α chain and at least a portion of an MHC class II β chain, such that said MHC class II α chain and β chains form a peptide binding groove; an antigenic peptide molecule; and an effector molecule. Suitable and preferred segments, peptides and linkers for use in the present invention are heretofore disclosed. A nucleic acid molecule of the present invention comprises at least one nucleic acid sequence encoding an MHC molecule, covalently attached (by base pair linkage) to at least one nucleic acid sequence encoding a linker, which is itself covalently attached (by base pair linkage) to at least one nucleic acid sequence encoding an antigenic peptide. The nucleic acid sequences are attached in such a manner that the sequences are transcribed in-frame, thereby producing a functional antigen-MHC class II molecule capable of forming a peptide binding site, alone or in combination with another MHC protein chain.

Preferred nucleic acid molecules encoding MHC class II compounds include: nucleic acid sequences encoding an MHC class II β chain, a linker and a spaceholder molecule, wherein the spaceholder molecule is linked to the class II β chain by the linker, and nucleic acid sequences encoding an MHC class II β chain, a linker and an antigenic peptide, wherein the peptide is linked to the class II β chain by the linker. A portion of each nucleic acid molecule encoding a component (i.e., an MHC class II component, a linker, or an antigenic peptide or an MHC class II component, a linker, or a spaceholder molecule) of an MHC class II compound can be covalently associated (using standard recombinant DNA methods) to any other sequence encoding at least a portion of a distinct component to produce an MHC class II compound of the present invention. A nucleic acid sequence encoding a linker is preferably covalently associated (by base pair linkage, e.g., ligated) to a nucleic acid sequence encoding an MHC class II component and encoding a linker. In one example, the 3' end (end encoding the C-terminus) of a nucleic acid molecule encoding an antigenic peptide of the present invention is ligated to the 5' end (end encoding the N-terminus) of a nucleic acid molecule encoding a linker of the present invention and the 3' end of the nucleic acid sequence encoding the linker is ligated to the 5' end of a nucleic acid molecule encoding an MHC class II compound.

In other embodiments, a nucleic acid sequence is used that encodes for a signal or leader segment that is capable of promoting secretion of an MHC class II compound from the cell that produces the molecule. Nucleic acid sequences encoding the leader or signal segments are covalently associated (by base pair linkage) to the 5' end of a nucleic acid molecule. The leader or signal segments can be segments which naturally are associated with an MHC molecule or are heterologous. Preferred segments are naturally associated segments.

The present invention also includes a recombinant molecule comprising a nucleic acid sequence encoding an MHC class II compound operatively linked to a vector capable of being expressed in a host cell. As used herein, "operatively linked" refers to insertion of a nucleic acid sequence into an expression vector in such a manner that the sequence is capable of being expressed when transformed into a host cell. As used herein, an "expression vector" is an RNA or DNA vector capable of transforming a host cell and effecting expression of an appropriate nucleic acid sequence, preferably replicating within the host cell. An expression vector can be either prokaryotic or eukaryotic, and typically is a virus or a plasmid.

Construction of desired expression vectors can be performed by methods known to those skilled in the art and expression can be in eukaryotic or prokaryotic systems. Prokaryotic systems typically used are bacterial strains including, but not limited to various strains of *E. coli*, various strains of bacilli or various species of Pseudomonas. In prokaryotic systems, plasmids are used that contain replication sites and control sequences derived from a species compatible with a host cell. Control sequences can include, but are not limited to promoters, operators, enhancers, ribosome binding sites, and Shine-Dalgarno sequences. Expression systems useful in eukaryotic host cells comprise promoters derived from appropriate eukaryotic genes. Useful mammalian promoters include early and late promoters from SV40 or other viral promoters such as those derived from baculovirus, polyoma virus, adenovirus, bovine papilloma virus or avian sarcoma virus. Expression vectors of the present invention include any vectors that function (i.e., direct gene expression) in recombinant cells of the present invention including bacterial, yeast, other fungal, insect, and mammalian cells. Particularly preferred expression vectors of the present invention include dual promoter baculovirus transfer vectors, and vectors containing class II promoters, β-actin promoters, globin promoters, or epithelial cell specific promoters.

An expression system can be constructed from any of the foregoing control elements operatively linked to the nucleic acid sequences of the present invention using methods known to those of skill in the art (see, for example, Sambrook et al., supra)

Host cells of the present invention can be: cells naturally capable of producing MHC protein; or cells that are capable of producing MHC protein when transfected with a nucleic acid molecule encoding an MHC protein. Host cells of the present invention include, but are not limited to bacterial, fungal, insect and mammalian cells. Suitable host cells include mammalian cells capable of stimulating a T cell response, preferably antigen presenting cells including dendritic cells, macrophages and B lymphocytes, as well as cells that are not capable of stimulating a T cell response, preferably fibroblasts, red blood cells, pluripotent progenitor cells, epithelial cells and neural cells.

In one aspect of the present invention, recombinant cells can be used to produce at least one MHC class II compound by culturing such cells under conditions effective to produce such molecules, and recovering the molecules. Effective conditions to produce a recombinant molecule include, but are not limited to appropriate culture media, bioreactor, temperature, pH and oxygen conditions. Depending on the expression vector used for production, resultant molecules can either remain within the recombinant cell, be retained on the outer surface of the recombinant cell, or be secreted into the culture medium. As used herein, the term "recovering the protein" refers to collecting the fermentation medium containing the protein and or recombinant cells. Recovery need not imply additional steps of separation or purification. MHC class II compounds of the present invention can be purified using a variety of standard protein purification techniques such as, but not limited to affinity chromatography, ion exchange chromatography, filtration, centrifugation, electrophoresis, hydrophobic interaction chromatography, gel filtration chromatography, chromatofocusing and differential solubilization. MHC class II compounds are preferably retrieved in "substantially pure" form. As used herein, "substantially pure" refers to a purity that allows for the effective use of the molecule as a heretofore described pharmaceutical composition or experimental reagent. Soluble MHC class II compounds of the present invention can be purified using, for example, affinity chromatography.

Therapeutic and Diagnostic Methods

The present invention provides for therapeutic methods of treating subjects (e.g., mammals, such as humans). In one aspect, the invention pertains to a method of treating an immune disorder, e.g., any disease, disorder, or condition which can be treated or prevented by modulating an immune response, e.g. through the modulation of an MHC class II-bearing T cell. As used herein, the term "immune disorder" includes any disease, disorder or condition which can be treated or prevented through the modulation, e.g., upregulation or down-regulation, of an immune response. In certain embodiments, the immune response is a Th-1-mediated immune response, such as a CTL-mediated immune response. In another embodiment, the immune response is a Th2-mediated immune response, such as an antibody-associated immune response. In certain embodiments, immune disorders include viral infections, bacterial infections, parasitic infections, autoimmune diseases, neoplastic disease, allergy as caused by allergens and toxicity.

The present invention also provides for diagnostic methods, wherein peptides that are capable of regulating an immune response, e.g., those peptides which regulate T cell activity, are screened. In another embodiment, methods are provided for the quantification of antigen-specific T cells in subjects suffering from an immune disorder. Such diagnostic methods may be used to monitor the progression of an immune disorder, such as HIV, in a subject, as well as to monitor the effectiveness of treatment, e.g., the methods may be repeated over the course of a therapeutic regiment. For example, in certain diseases, such as HIV, disease progression and the effectiveness of therapy may be quantified by measuring the quantity of $CD4^+$ T cells in the subject.

A general principle of the diagnostic methods of the present invention involves isolating peripheral T cells from a subject suffering from an immune disorder e.g., infectious diseases, autoimmune diseases, allergy, neoplastic diseases and toxicity. There are many established methods for the isolation of peripheral blood T cells from a subject. For example, one method involves drawing blood from a subject and isolating peripheral blood mononuclear cells (PBMCs) by Ficoll-Hypaque™ (Pharmacia) centrifugation. Peripheral blood T cells can then be isolated and purified by rosetting the peripheral blood T cells with sheep red blood cells. The purified T cells can then be cultured in vitro with an MHC class II compound of the present invention.

In a particular embodiment, peptides are screened (e.g., identified) that are capable of regulating an immune response by (a) culturing an MHC class II compound with at least one isolated T cell, wherein the MHC class II compound comprises (i) an MHC class II component comprising at least a portion of an MHC class II α chain and an MHC class II β chain, such that the MHC class II α chain and MHC class II β chain form a peptide binding groove; (ii) an antigenic peptide molecule, wherein the antigenic peptide molecule binds within said peptide binding groove; and (iii) an effector component, wherein the effector component is linked to the MHC class II component, such that the isolated T cell is capable of recognizing and binding to the MHC class II compound to form an MHC class II compound-T cell complex; (b) isolating the complex; and (c) assaying the complex to identify the antigen-specific T cell. The methods of the present invention can thus be used to identify and characterize specific antigens which are recognized by the subject suffering from the immune disorder. Several assays are known in the art that may be used to identify and characterize the antigen-T cell complex, including, but not limited to, enzyme-linked immunosorbant assays (ELISA) or cell growth assays to detect cytokine production by the T cell and Western and Northern blotting to determine if protein and/or mRNA expression is altered, respectively. Quantification of antigen-MHC class II compound complexes can be ascertained using routine techniques, such as flow cytometric analysis.

In another embodiment of the present invention, peripheral blood T cells that are isolated from a subject suffering from an immune disorder, e.g., HIV, are (a) cultured at the onset of infection and at different times during the course of therapy with an MHC class II compound, wherein the MHC class II compound comprises (i) an MHC class II component comprising at least a portion of an MHC class II α chain and an MHC class II β chain, such that the MHC class II α chain and MHC class II β chain form a peptide binding groove; (ii) an antigenic peptide molecule, wherein the antigenic peptide molecule binds within said peptide binding groove; and (iii) an effector component, wherein the effector component is linked to the MHC class II component, such that the isolated T cell is capable of recognizing and binding to the MHC class II compound to form an MHC class II compound-T cell complex; (b) isolating the complex; and (c) assaying the complex to identify the antigen-specific T cell. The methods of the present invention are therefore useful for the identification, characterization and quantification of antigen-specific T cells from a subject.

As used herein, the term "viral infection" includes infections with organisms including, but not limited to, HIV (e.g., HIV-1 and HIV-2), human herpes viruses, cytomegalovirus (esp. Human), Rotavirus, Epstein-Barr virus, Varicella Zoster Virus, hepatitis viruses, such as hepatitis B virus, hepatitis A virus, hepatitis C virus and hepatitis E virus, paramyxoviruses: Respiratory Syncytial virus, parainfluenza virus, measles virus, mumps virus, human papilloma viruses (for example HPV6, 11, 16, 18 and the like), flaviviruses (e.g. Yellow Fever Virus, Dengue Virus, Tick-borne encephalitis virus, Japanese Encephalitis Virus) or influenza virus.

As used herein, the term "bacterial infections" include infections with a variety of bacterial organisms, including gram-positive and gram-negative bacteria. Examples include, but are not limited to, *Neisseria* spp, including *N. gonorrhea* and *N. meningitidis, Streptococcus* spp, including *S. pneumoniae, S. pyogenes, S. agalactiae, S. mutans; Haemophilus* spp, including *H. influenzae* type B, non typeable *H. influenzae, H. ducreyi; Moraxella* spp, including *M catarrhalis*, also known as *Branhamella catarrhalis; Bordetella* spp, including *B. pertussis, B. parapertussis* and *B. bronchiseptica; Mycobacterium* spp., including *M. tuberculosis, M. bovis, M. leprae, M. avium, M. paratuberculosis, M. smegmatis; Legionella* spp, including *L. pneumophila; Escherichia* spp, including enterotoxic *E. coli*, enterohemorragic *E. coli*, enteropathogenic *E. coli; Vibrio* spp, including *V. cholera, Shigella* spp, including *S. sonnei, S. dysenteriae, S. flexnerii; Yersinia* spp, including *Y. enterocolitica, Y. pestis, Y. pseudotuberculosis, Campylobacter* spp, including *C. jejuni* and *C. coli; Salmonella* spp, including *S. typhi, S. paratyphi, S. choleraesuis, S. enteritidis; Listeria* spp., including *L. monocytogenes; Helicobacter* spp, including *H. pylori; Pseudomonas* spp, including *P. aeruginosa, Staphylococcus* spp., including *S. aureus, S. epidermidis; Enterococcus* spp., including *E. faecalis, E. faecium; Clostridium* spp., including *C. tetani, C. botulinum, C. difficile; Bacillus* spp., including *B. anthracis; Corynebacterium* spp., including *C. diphtheriae; Borrelia* spp., including *B. burgdorferi, B. garinii, B. afzelii, B. andersonii, B. hermsii; Ehrlichia* spp., including *E. equi* and the agent of the Human Granulocytic Ehrlichiosis; *Rickettsia* spp., including *R. rickettsii; Chlamydia* spp., including *C. trachomatis, C. neumoniae, C. psittaci; Leptsira* spp., including *L. interrogans; Treponema* spp., including *T. pallidum, T. denticola, T. hyodysenteriae*. Preferred bacteria include, but are not limited to, *Listeria*, mycobacteria, mycobacteria (e.g., tuberculosis), Anthrax, *Salmonella* and *Listeria* monocytogenes.

As used herein, the term "autoimmunity" refers to the condition in which a subject's immune system starts reacting against his or her own tissues. Non-limiting examples of autoimmune diseases and disorders having an autoimmune component that may be treated according to the invention include type 1 diabetes, arthritis (including rheumatoid arthritis, juvenile rheumatoid arthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, iritis, conjunctivitis, keratoconjunctivitis, ulcerative colitis, asthma, allergic asthma, cutaneous lupus erythematosus, scleroderma, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. In preferred embodiments, the disease is selected from the group consisting of type 1 diabetes, multiple sclerosis and rheumatoid arthritis.

As used herein, the term "parasitic infection" includes infections with a variety of protozoal and parasitic organisms such as, but not limited to, Anaplasma, Babesia, Balantidium, Besnoitia, Chlamydia, Coccidia, Cryptospondium, Cytauxzoon, Eimeria Entamoeba, Eperythrozoon, Erlichia, Giardia, Haemobartonella, Hammondia, Isopora, Leishmania, Neorickettsia, Plasmodium, Pneumocystis, Rickettsia, Schistosoma, Sarcocystis, Theileria, Thrichinella, Toxoplasma, Trichomonas, Trypanosoma, Unicaria, Dipylidium, Echinococcuse, Taenia, Ancylostoma, Ascaris, Enterobius, Strongyloides, Strongylus, Toxocara, Toxascaris and Trichuris. The method is particularly useful for treating blood-borne protozoal and parasitic diseases.

As used herein, the term "allergy" refers to the state of hypersensitivity induced by exposure to a particular antigen (allergen) which results in harmful immunologic reactions on subsequent exposures. Examples of allergens include, but are not limited to, plant, animal, bacterial, and parasitic allergans as well as metal-based allergens that cause contact sensitivity. Other allergans include weed, grass, tree, peanut, mite, flea and cat antigens.

As used herein, the term "toxicity" refers to the quality of being poisonous, i.e. that caused by a poison or toxin. As used in the art, this term also refers to the degree of virulence of a toxic microbe or of a poison. By "toxin" it is meant a poisonous substance of biological origin, which necessarily excludes synthetic toxins which contain no contaminating DNA. The toxins are usually, but are not necessarily, proteins. The methods of the present invention for treating and preventing a toxin-related SPF disorder are effective for preventing, treating or eliminating toxicity caused by a variety of toxins Nonlimiting examples of protein toxins include botulin, perfringens toxin, mycotoxins, shigatoxins, staphylococcal enterotoxin B, tetanus, ricin, cholera, aflatoxins, diphtheria, T2, seguitoxin, saxitoxin, abrin, cyanoginosin, alphatoxin, tetrodotoxin, aconotoxin, snake venom, scorpion venom and other spider venoms. A nonlimiting example of a non-protein toxin is tricothecene (T-2). Toxin-producing microorganisms of interest include, but are not limited to: *Corynebacterium diphtheriae*, Staphylococci, *Salmonella typhimuium*, Shigellae, *Pseudomonas aeruginosa, Vibrio cholerae, Clostridium botulinum*, and *Clostridium tetani*. A nonlimiting example of a toxin producing plant is *Ricinus comnunis*, and of a fungus producing a toxin is *Aspergillus favus*.

As used herein, the term "neoplastic disease" is characterized by malignant tumor growth or in disease states characterized by benign hyperproliferative and hyperplastic cells. The common medical meaning of the term "neoplasia" refers to "new cell growth" that results as a loss of responsiveness to normal growth controls, e.g., neoplastic cell growth.

As used herein, the terms "hyperproliferative", "hyperplastic", malignant" and "neoplastic" are used interchangeably, and refer to those cells in an abnormal state or condition characterized by rapid proliferation or neoplasia. The terms are meant to include all types of hyperproliferative growth, hyperplastic growth, cancerous growths or oncogenic processes, metastatic tissues or malignantly transformed cells, tissues, or organs, irrespective of histopathologic type or stage of invasiveness. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be either benign, premalignant or malignant.

The terms "neoplasia," "hyperplasia," and "tumor" are often commonly referred to as "cancer," which is a general name for more than 100 disease that are characterized by uncontrolled, abnormal growth of cells. Examples of cancer include, but are not limited to: breast; colon; non-small cell lung, head and neck; colorectal; lung; prostate; ovary; renal; melanoma; and gastrointestinal (e.g., pancreatic and stomach) cancer; and osteogenic sarcoma.

The term "tumor antigen" as used herein relates to any antigen expressed on a tumor cell, including but not limited to, Mucin1, carcinoembryonic antigen, oncofetal antigens and tumor-associated antigens. Also included in this definition are any antigens expressed by tumor cells that are encoded by a single DNA strand.

The terms "induce", "inhibit", "potentiate", "elevate", "increase" "decrease" or the like, denote quantitative differences between two states, refer to at least statistically significant differences between the two states. For example, "an amount effective to inhibit growth of hyperproliferative cells" means that the rate of growth of the cells will at least statistically significantly different from the untreated cells. Such terms are applied herein to, for example rates of cell proliferation.

In one embodiment, the present invention includes administering to a subject having an immune disorder, an effective amount of an MHC class II compound of the present invention, thereby treating the immune disorder in the subject.

Also within the scope of this invention is to administer an MHC class II compound prophylactically. Administration of an MHC class II compound of the present invention can occur prior to the manifestation of symptoms of an immune disorder, such that the disorder is prevented or, alternatively, delayed in its progression. The prophylactic methods of the present invention can be carried out in a similar manner to therapeutic methods described herein, although dosage and treatment regimens may differ.

Accordingly, the present method has therapeutic utility in modulating an MHC class II-restricted T cell. In one embodiment, the present method has therapeutic utility in biasing an immune response towards a Th1-mediated (i.e. cell-mediated) immune response depending upon the desired therapeutic regimen. As used herein, a "type-1 immune response", also referred to herein as a "type-1 response" or a "T helper type 1 (Th1) response" includes a response by CD4+ T cells that is characterized by the expression, production or secretion of one or more type-1 cytokines and that is associated with delayed type hypersensitivity responses. The phrase "type-1 cytokine" includes a cytokine that is preferentially or exclusively expressed, produced or secreted by a Th1 cell, that favors development of Th1 cells and/or that potentiates, enhances or otherwise mediates delayed type hypersensitivity reactions. Preferred type-1 cytokines include, but are not limited to, GM-CSF, IL-2, IFN-γ, TNF-α, IL-12, IL-15 and IL-18.

In another embodiment, the present invention has therapeutic utility in biasing an immune response towards a Th2-mediated (i.e. antibody-associated immunity). As used herein, a "type-2 immune response", also referred to herein as a "type-2 response" or a "T helper type 2 (Th2) response" refers to a response by CD4+ T cells that is characterized by the production of one or more type-2 cytokines and that is associated with humoral or antibody-associated immunity (e.g., efficient B cell, "help" provided by Th2 cells, for example, leading to enhanced IgG1 and/or IgE production). The phrase "type-2 cytokine" includes a cytokine that is preferentially or exclusively expressed, produced or secreted by a Th2 cell, that favors development of Th2 cells and/or that potentiates, enhances or otherwise mediates antibody production by B lymphocytes. Preferred type-2 cytokines include, but are not limited to, IL-4, IL-5, IL-6, IL-10, and IL-13. Such methods are particularly useful in diseases such as viral infections (e.g., Ebola, Hepatitis C, HIV and RSV), bacterial infections (e.g., anthrax, *Listeria* monocytogenes, *Legionella* and *mycobacterium* tuberculosis), parasitic infections (e.g., malaria), toxicity (e.g., *shigella* toxin, toxin botulinum and tetanus toxin), autoimmune disorders (e.g., type I diabetes mellitus and multiple sclerosis), and neoplastic diseases (e.g., breast, colon, non-small cell lung, head and neck, colorectal, lung, prostate, ovary, renal, melanoma, gastrointestinal (e.g., pancreatic and stomach) cancer and osteogenic sarcoma).

Also within the scope of the invention are methods of regulating an immune response ex vivo comprising the steps of isolating a T cell population from a subject, contacting the T cell population with an effective amount of an isolated MHC class II compound of the present invention, and re-administering the T cell population back into the subject, thereby regulating the immune response.

Moreover, the invention also provides for a method of treating an immune disorder in a subject ex vivo comprising the steps of isolating a T cell population from a subject, contacting the T cell population with an effective amount of an isolated MHC class II compound of the present invention, and re-administering the T cell population back into the subject, thereby treating the immune disorder in the subject.

Pharmaceutical Compositions and Uses Thereof

Another aspect of the invention provides pharmaceutically-acceptable compositions which comprise an MHC class II compound of the present invention and a pharmaceutically-acceptable carrier(s), in an amount effective to modulate an immune response.

In one embodiment, the MHC class II compound is administered to the subject using a pharmaceutically-acceptable formulation, e.g., a pharmaceutically-acceptable formulation that provides sustained delivery of the MHC class II compound to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

As used herein, the term "effective amount" includes an amount effective, at dosages and for periods of time necessary, to achieve the desired result, e.g., sufficient to modulate an immune response. An effective amount of an MHC class II compound, as defined herein may vary according to factors such as the disease state, age, and weight of the subject, and the ability of the MHC class II compound to elicit a desired response in the subject. Dosage regimens may be adjusted to provide the optimum therapeutic response. An effective amount is also one in which any toxic or detrimental effects (e.g., side effects) of the MHC class II compound of the present invention are outweighed by the therapeutically beneficial effects.

A therapeutically effective amount of an MHC class II compound (i.e., an effective dosage) may range from about 0.001 to 30 µg/kg body weight, preferably about 0.01 to 25 µg/kg body weight, more preferably about 0.1 to 20 µg/kg body weight, and even more preferably about 1 to 10 µg/kg, 2 to 9 µg/kg, 3 to 8 µg/kg, 4 to 7 µg/kg, or 5 to 6 µg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an MHC class II compound can include a single treatment or, can include a series of treatments. In one example, a subject is treated with an MHC class II compound in the range of between about 0.1 to 20 µg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of an MHC class II compound used for treatment may increase or decrease over the course of a particular treatment.

The methods of the invention further include administering to a subject a therapeutically effective amount of an MHC class II compound in combination with another pharmaceutically active compound known to modulate cell-mediated immune responses, e.g., agents such as interleukins (IL) (e.g. IL-2, IL-12, IL-15), lipopolysaccharide (LPS), concanavalin A (ConA), phorbol esters, and ionomycin. Alternatively, the MHC class II compound of the present invention may also be administered in combination with another pharmaceutically active compound known to modulate Th2-mediated immune responses, e.g., agents such as IL-4, IL-10 and IL-13. Other pharmaceutically active compounds that may be used can be found in Harrison's Principles of Internal Medicine, Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. The MHC class II compound and the pharmaceutically active compound may be administered to the subject in the same pharmaceutical composition or in different pharmaceutical compositions (at the same time or at different times).

The regimen of administration also can affect what constitutes an effective amount. MHC class II compound of the present invention can be administered to the subject prior to, simultaneously with, or after the administration of the other agent(s). Further, several divided dosages, as well as staggered dosages, can be administered daily or sequentially, or the dose can be proportionally increased or decreased as indicated by the exigencies of the therapeutic situation.

The phrase "pharmaceutically acceptable" is employed herein to refer to those MHC class II compounds of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing an MHC class II compound include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these compositions include the step of bringing into association an MHC class II compound with the carrier and, optionally, one or more accessory ingredients. In general, the formulations are prepared by uniformly and intimately bringing into association an MHC class II compound with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an MHC class II compound(s) as an active ingredient. An MHC class II compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the MHC class II compound(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active MHC class II compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more MHC class II compound(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of an MHC class II compound(s) include powders, sprays, ointments, pastes, creams, lotions, gels, solutions, patches and inhalants. The active MHC class II compound(s) may be mixed under sterile conditions with a pharmaceutically-acceptable carrier, and with any preservatives, buffers, or propellants which may be required. The ointments, pastes, creams and gels may contain, in addition to MHC class II compound(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an MHC class II compound(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The MHC class II compound(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (TWEEN®, PLURONIC®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of an MHC class II compound(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of this invention.

Pharmaceutical compositions of this invention suitable for parenteral administration comprise one or more MHC class II compound(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of MHC class II compound(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the MHC class II compound(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

The term "administration" or "administering" is intended to include routes of introducing the MHC class II compound(s) to a subject to perform their intended function. Examples of routes of administration which can be used include injection (subcutaneous, intravenous, parenterally, intraperitoneally, intrathecal), oral, inhalation, rectal and transdermal. The pharmaceutical preparations are, of course, given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the MHC class II compound can be coated with or disposed in a selected material to protect it from natural conditions which may detrimentally affect its ability to perform its intended function. The MHC class II compound can be administered alone, or in conjunction with either another agent as described above or with a pharmaceutically-acceptable carrier, or both. The MHC class II compound can be administered prior to the administration of the other agent, simultaneously with the agent, or after the administration of the agent. Furthermore, the MHC class II compound can also be administered in a proform which is converted into its active metabolite, or more active metabolite in vivo.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of an MHC class II compound(s), drug or other material, such that it enters the subject's system and, thus, is subject to metabolism and other like processes, for example, subcutaneous administration.

Regardless of the route of administration selected, the MHC class II compound(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of this invention may be varied so as to obtain an amount of the active ingredient which is effective to achieve the desired therapeutic response for a particular subject, composition, and mode of administration, without being toxic to the subject. An exemplary dose range for a human subject is from about 0.1 to about 10 mg per day.

A preferred dose of the MHC class II compound for the present invention is the maximum that a subject can tolerate and not develop serious hypercalcemia. In one embodiment, the MHC class II compound of the present invention is administered at a concentration of about 0.001 µg to about 100 µg per kilogram of body weight, about 0.001-about 10 µg/kg or about 0.001 µg-about 100 µg/kg of body weight. Ranges intermediate to the above-recited values are also intended to be part of the invention.

The following experimental results are provided for purposes of illustration only and are not intended to limit the scope of the invention.

EXAMPLES

1. Example 1

This example illustrates the development of MHC class II tetramers that are based on the cellular peptide loading mechanism of the present invention. The results show that peptides from HIV p24 protein were identified that bound to multiple allelic forms of HLA-DR and represented immunodominant T cell epitopes. These tetrameric forms of HLA-DR DR/HIV p24 complexes were able to label expanded populations of CD4+ T cells directly ex vivo in patients who had been treated during the acute stage of infection.

Materials and Methods

A. Expression of DR/CLIP Precursors

The constructs for the expression of DR/CLIP complexes were based on those previously described for DR2 (DRA, DRB1*1501), which carried Fos and Jun dimerization domains (see, e.g., Gauthier, L. et al. (1998) *Proc. Natl. Acad. Sci., USA* 95:11828). For the β chain constructs (DRB1*0101, DRB1*0401, DRB1*1501, DRB5*0101), the covalently linked myelin basic protein (MBP) peptide was replaced with the Class II-associated invariant chain peptide (CLIP; PVSKMRMATPLLMQA (SEQ ID NO:1), single amino acid code). For the DRα chain construct, a BirA biotinylation site (GLNDIFEAQKIEWHE (SEQ ID NO:6)) was attached via a six amino acid linker (GGSGGS (SEQ ID NO:7)) to the 3' end of the Fos dimerization domain (see, e.g., Beckett, D. et al. (1999) *Protein Sci.* 8:921). The four different DRβ chain constructs were co-transfected with the DRα chain construct into CHO-K1 cells (ATCC, Manassas, Va.) using the Effectene™ kit (Qiagen, Valencia, Calif.). Clones were screened for secretion of DR molecules in an ELISA using the monoclonal antibody (mAb) L243 (ATCC) and polyclonal DR serum (see, e.g., Kalandadze, A. et al. (1996) *J. Biol. Chem.* 271:20156) for capture and detection, respectively. Clones with the highest expression levels were expanded for inoculation into bioreactors. For large-scale protein production, the ACUSYST-miniMAX™ instrument (Cellex Biosciences, Minneapolis, Minn.) was used, which allows control of temperature, pH and media feed rate. Transfectants were grown in hollow fiber reactors with an internal surface area of 1.1 m² and supernatants from the extracellular space were harvested by the instrument at a predetermined flow rate into a collection bottle placed at 4° C. These cultures were maintained for approximately three months, and supernatants were frozen at weekly intervals. DR molecules were purified by affinity chromatography with mAb L243 (ATCC) as described by Gauthier et al. (supra).

B. Processing of DR Molecules: Biotinylation, Thrombin Cleavage, and Peptide Exchange Purified DR molecules were biotinylated using a 1:20 molar ratio of BirA to DR in a buffer containing 100 μM biotin, 10 mM ATP, 10 mM magnesium acetate, 50 mM bicine and 1× protease inhibitor cocktail (Sigma, St. Louis, Mo.) at pH 8.0. The final HLA-DR concentration was adjusted to 2.5 mg/ml with 10 mM Tris, pH 8.0 and the reaction was incubated overnight at 30° C. The protein was then extensively dialyzed against PBS to remove any free biotin. Biotinylation was confirmed by electrophoresis on native polyacrylamide gels (SDS-PAGE) (6%) and dimers, trimers and tetramers of DR molecules could be visualized at different molar ratios of streptavidin and DR.

Prior to the peptide exchange reaction, the linker was cleaved with thrombin to allow release of the CLIP peptide. Twenty (20) units of thrombin (Novagen, Madison, Wis.) per milligram for DRB1*0101 and DRB1*0401 molecules, and 40 units per milligram for DRB5*0101 and DRB1*1501, were used. Reactions were incubated at room temperature for 2 hours and thrombin was then inactivated by addition of Pefabloc™ (final concentration of 1 mg/ml, Roche, Indianapolis, Ind.). Thrombin cleavage was confirmed by SDS-PAGE based in a shift in the molecular weight of the DRβ chain. Thrombin-cleaved complexes are designated as *DR/CLIP. Peptide exchange was performed using dinitrophenol (DNP)-labeled peptides for affinity purification of defined DR/peptide complexes. The DNP group was attached to the N-terminus of peptides via an aminohexanoic acid (Ahx) linker during synthesis (New England Peptide, Fitchburg, Mass.). All peptides were HPLC purified and analyzed by mass spectrometry.

Peptide loading was carried out with 3.3 μM *DR/CLIP and 50 μM of the respective DNP-labeled peptide in a buffer containing 50 mM sodium citrate, pH 5.2, 1% octylglucoside, 100 mM NaCl, and 1× protease inhibitor cocktail (Sigma). The reactions were incubated overnight at 30° C. and then concentrated by ultrafiltration. The *DR/CLIP concentration and reaction temperature were chosen based on preliminary experiments designed to minimize aggregation of empty DR molecules created by CLIP dissociation. Aggregation was substantially lower at *DR/CLIP concentrations on 3.3 μM as compared to 8.25 μM, and at a reaction temperature of 30° C. rather than 37° C. DR molecules were separated from unbound peptide using a Superose™ 12 high performance liquid chromatography (HPLC) gel filtration column (Amersham Pharmacia Biotech, Piscataway, N.J.) using PBS at a flow rate of 0.8 ml/min. The peak representing DR molecules was collected and injected onto an anti-DNP HPLC affinity column. The anti-DNP affinity column was generated by covalently cross-linking 10 mg of anti-DNP-1 antibody (Biotrend Chemikalien, Cologne, Germany) to a 4.6 mm×50 mm protein G column on POROS 20 XL™ media (Applied Biosystems, Foster City, Calif.). DR molecules with bound DNP-peptide were eluted from the column using 50 mM CAPS, pH 11.5 and eluates were neutralized by addition of 1 M phosphate, pH 6.0. Biotinylated, peptide loaded DR molecules were concentrated by ultrafiltration (Centrion™ 2 ml concentrator, Millipore, Bedford, Mass.) and the buffer was simultaneously changed to PBS. Biotinylated DR/peptide complexes were frozen in small aliquots at −80° C. and multimerized with labeled streptavidin prior to use in staining reactions C. Kinetics of CLIP Dissociation and Peptide Association To study the kinetics of CLIP dissociation and HA peptide association, 8.33 μM of *DR/CLIP was incubated overnight at 37° C. with 100 nM Alexa 488-labeled CLIP peptide in 50 mM sodium citrate, pH 5.2, 1% octyglucoside, 100 mM NaCl, and 1× protease inhibitor cocktail (Sigma). A molar excess of the high affinity influenza HA peptide (amino acids 306-318; SEQ IS NO:15) was then added, and the reactions were incubated for different periods of time at 37° C. and then frozen until analysis. Complexes of DR- and Alexa 488-labeled peptide (SEQ ID NO:8) were separated from unbound peptide using a Bio-Silect™ SEC-125 gel filtration column (Bio-Rad, Hercules, Calif.) run at a flow rate of 1 ml/min with PBS. The Alexa 488-labeled peptide (SEQ ID NO:8) was detected using a HPLC fluorescence detector with excitation and emission wavelengths set at 495 and 519 nm, respectively (Varian ProStar 363, Varian Analytical Instruments, Walnut Creek, Calif.). Peptide association was examined using 3.3 μM *DR/CLIP and 50 μM Alexa 488-labeled influenza HA peptide (SEQ ID NO:9), using the same conditions as described above. The amount of bound peptide was determined based in the surface area of the peak that represented the DR/peptide complex. Half-life for dissociation was calculated by fitting data to an equation describing an exponential decay. Half-life for association was calculated by fitting data to an equation describing exponential rise. The following labeled peptides were used in these experiments:

CLIP (87-101) Alexa 488: CGGGPVSKMRMATPLLMQA (SEQ ID NO:8) and influenza HA (306-318) Alexa 488: CGGGPKYVKQNTLKLAT (SEQ ID NO:9).

D. Peptide Binding Assay

Competition assays were performed to identify peptides from the human immunodeficiency virus (HIV) p24 antigen that would be suitable for tetramer production. Twenty-three (23) overlapping peptides (22-mers, 12 amino acid overlaps) that covered the HIV p24 sequence were used as competitors for binding of labeled peptides to DR/CLIP complexes. Unlabeled HIV p24 competitor peptides were tested at concentrations ranging from 30 nM to 30 µM in the presence of 30 nM of labeled peptides and DR/CLIP at 1.7 µM. A biotinylated MBP (amino acids 85-99; SEQ ID NO:26)) peptide was used for DRB1*1501 molecules, and a DNP-labeled HA (amino acids 306-318; SEQ ID NO:9) peptide for the other three molecules (DRB1*0101, DRB1*0401, DRB5*0101). Reactions were incubated for 20 hours at 37° C. in 50 mM sodium citrate, pH 5.2, 1% octylglucoside, 100 mM NaCl, 100 µg/ml of bovine serum albumin (BSA) and 1× protease inhibitor cocktail (Sigma). Next, 100 ng of DR was loaded onto a 96-well plate (Wallac) coated with 200 ng/well of mAb L243. DNP-labeled peptide bound to DR molecules was detected with biotinylated anti-DNP-1 antibody, followed by europium-labeled streptavidin. The biotinylated anti-DNP-1 was omitted for detection of DR-bound biotinylated MBP (amino acids 85-99; SEQ ID NO:26) peptide. Fluorescence was quantified using a Delfia™ 1234 fluorometer, as previously described by Hausmann, D. H. et al. (Hausmann, D. H. et al. (1999) J. Exp. Med. 189:1723).

Five (5) HIV p24 peptides were selected for the generation of tetramers, and peptide binding motifs were used to select 13-15 amino acid segments within the 22 amino acid sequences (see Table 1). All peptides were synthesized with an N-terminal DNP group and Ahx linker. The synthesized peptides are as follows: p24-1 DNP-(Ahx)YKRWI-ILGLNKIV (SEQ ID NO:10); p24-2 DNP-(Ahx)-LNKIVRMYSPTSI (SEQ ID NO:11); p24-3 DNP-(Ahx)-SPEVIPMFSALSEG (SEQ ID NO:12); p24-4 DNP-(Ahx)-DRFYKTLRAEQASQ (SEQ ID NO: 13); p24-5 DNP-(Ahx)-EQIGWMTNNPPIPVG (SEQ ID NO: 14). A number of other peptides were used as positive and negative controls: influenza HA (306-318) DNP-(Ahx)-PKYVKQNTLKLAT (SEQ ID NO: 15); gP100 (44-59) DNP-(Ahx)-WNRQ-LYPEWTEAQRLD (SEQ ID NO: 16); annexin 11 (208-223) DNP-(Ahx)-DVPKWISIMTERSVPH (SEQ ID NO: 17); and MBP (88-102) DNP-(Ahx)-VVHFFKNIVTPRTPP (SEQ ID NO: 18).

TABLE 1

Identification of HIV p24 Peptides that Bind to Multiple HLA-DR Molecules

| Peptides | IC$_{50}$ of peptides (µM) | | | |
|---|---|---|---|---|
| | DRB1*0101 | DRB5*0101 | DRB1*1501 | DRB1*0401 |
| HA (306-318) | 0.22 | 0.55 | — | 0.3 |
| MBP (85-99) | — | — | 0.3 | — |
| p24 (1-22) | — | — | 8.0 | — |
| p24 (11-32) | — | — | — | — |
| p24 (21-42) | — | — | — | — |
| p24 (31-52) | 2.3 | 10.5 | 0.68 | 0.7 |
| p24 (41-62) | — | — | — | — |
| p24 (51-72) | — | — | 10.8 | — |
| p24 (61-82) | — | — | — | — |
| p24 (71-92) | — | — | — | — |
| p24 (81-102) | — | — | — | — |
| p24 (91-112) | — | — | — | — |
| p24 (101-122) | — | — | — | — |
| p24 (111-132) | — | — | 10.8 | 5.0 |
| p24 (121-142) | — | 11.5 | 11.0 | — |
| p24 (131-152) | 1.9 | 10.5 | 0.22 | 3.0 |
| p24 (141-162) | — | — | — | — |
| p24 (151-172) | — | — | — | — |
| p24 (161-182) | 4.5 | 2.0 | 9.0 | 2.0 |
| p24 (171-192) | — | — | 0.9 | — |
| p24 (181-202) | — | — | — | — |
| p24 (191-212) | 1.6 | — | 3.0 | — |
| P24 (201-222) | — | — | — | — |
| p24 (211-232) | — | — | — | — |
| p24 (221-242) | — | — | — | — |

E. Generation of T Cell Lines Specific for the Influenza HA Peptide

Blood mononuclear cells from normal donors with the appropriate DR subtype were plated at 2×10⁵ cells/well in 96-well U-bottom plates in the presence of influenza HA (306-318) peptide (0.2 to 1.0 µM) and RPMI 1640, 10% human serum, 2 mM L-glutamine, 10 mM HEPES, and 100 µg/ml penicillin/streptomycin. Recombinant IL-2 was added after three days to a final concentration of 5 units/ml (Roche), and half of the media was changed every three (3) days. Cell lines were maintained by restimulation with autologous irradiated mononuclear cells and HA peptide at 10 to 14 day intervals as described by Wucherpfennig et al. ((1994) J. Exp. Med. 179:279).

F. Labeling of T Cells with MHC Class II Tetramers

For HIV tetramer formation, biotinylated DR/peptide complexes were incubated with R-phycoerythrin-labeled streptavidin (Molecular Probes, Eugene, Oreg.) for at least one (1) hour on ice, at a 4:1 molar ratio of DR to streptavidin and a final DR concentration of 0.2 mg/ml. For analysis of blood lymphocytes from patients infected with HIV, CD4+ T cells were enriched using the CD4⁺ RosetteSep™ reagent (StemCell Technologies, Vancouver, BC, Canada). This process results in binding of unwanted cell populations to red blood cells, which pellet during FICOLL® density gradient centrifugation. Four-color FACS analyses (Using a FACSCalibur™ machine (Becton Dickinson) and CellQuest™ software) was performed with the PE-labeled tetramer and antibodies to CD3 (FITC-labeled), CD4 (PerCP-labeled), and CD25 (APC-labeled) (all acquired from BD Pharmingen, San Diego, Calif.), which allowed gating on the CD3⁺ population and analysis of CD4⁺ or CD25' versus tetramer staining Isolated CD4⁺ T cells were stained with tetramers (typically at 10 µg/ml) in RPMI, 10% human serum for one hour at 37° C. in the presence of labeled antibodies, washed twice and fixed in 1% formaldehyde/PBS. For staining of T cell lines, monocytes were depleted by FICOLL® density gradient centrifugation with a CD4⁺ enrichment cocktail (StemCell Technologies) and staining was performed with 100 µl of PBS with 2% fetal calf serum in the presence of tetramers and labeled antibodies. Lymphocytes were gated based on forward and side scatter and CD3 expression. Multiple control tetramers with irrelevant peptides were used in most experiments to demonstrate specificity of binding by the relevant tetramers (see Table 2).

TABLE 2

Efficiency of Peptide Loading for Different HLA-DR Molecules

|  | MHC Peptide | (μM) | Loading Efficiency (%) |
|---|---|---|---|
| DRB1*0101 | HA(306-318) | 0.25 | 100 |
|  | p24 (33-46) | 2.3 | 80 |
|  | p24 (138-150) | 1.9 | 53 |
|  | p24 (166-179) | 4.5 | 100 |
| DRB5*0101 | HA(306-318) | 0.55 | 80 |
|  | p24 (166-179) | 2.0 | 79 |
| DRB1*1501 | MBP(85-99) | 0.3 | ND |
|  | p24 (33-46) | 0.68 | 63 |
|  | p24 (138-150) | 0.22 | 59 |
| DRB1*0401 | HA(306-318) | 0.3 | 100 |
|  | gp100(45-59) | 5 | 95 |
|  |  | 1.1 | 99 |
|  | MBP(88-102) | 0.3 | 92 |
|  | p24 (33-46) | 0.7 | 87 |
|  | p24 (113-127) | 5.0 | 79 |
|  | p24 (138-150) | 3.0 | 90 |
|  | p24 (138-150)/Val | 3.0 | 90 |
|  | p24 (166-179) | 2.0 | 99 |

Results

A. Expression of DR/CLIP Precursors in Mammalian Cells

The present invention describes a novel approach for the generation of MHC class II tetramers that is based on the cellular peptide exchange mechanism. In antigen presenting cells, MHC class II molecules assemble in the ER with an invariant chain and the CLIP segment of the invariant chain serves to protect the hydrophobic binding site. Following transport to the endosomal/lysosomal peptide-loading compartment, invariant chain is proteolytically cleaved and the remaining CLIP peptide is exchanged with other peptides in a reaction catalyzed by HLA-DM (Sherman, M. A., et al. (1995) *Immunity* 3:197; Sloan, V. S., et al. (1995) *Nature* 375:802; Roche, P. A., and Cresswell, P. (1990) *Nature* 345:615; Riberdy, J. M., et al. 1992. *Nature* 360:474; Denzin, L. K., and Cresswell, P. (1995) *Cell* 82:155). This cellular peptide exchange mechanism thus preserves the functionality of MHC class II molecules prior to exposure to peptides in the appropriate cellular compartment. The CLIP peptide (SEQ ID NO: 1) binds to all human and murine MHC class II molecules, thus making it particularly useful in the present invention (see, e.g., Malcherek, G. et al. (1995) *J. Exp. Med.* 181:527 and Riberdy, J. M. et al. (1992) *Nature* 360:474). Four different HLA-DR molecules were expressed with the bound CLIP peptide: HLA-DR1 (DRA, DRB1*0101), HLA-DR2a (DRA, DRB5*0101), HLA-DR2b (DRA, DRB1*1501) and HLA-DR4 (DRA, DRB1*0401). A schematic representation of the CLIP peptide covalently associated with the binding site of an MHC class II molecule is shown in FIG. 1A. These alleles were chosen because of their commonality among different ethnic groups and their relevance in chronic inflammatory diseases. Leucine zipper dimerization domains from the transcription factors Fos and June were attached to the 3' end of the DRα and DRβ ectodomains, as previously described (see generally, e.g., Kalandadze, A. et al. (supra); Scott C. A. et al. (1996) *J. Exp. Med.* 183:2087; Hausmann, D. H. et al. (1999) *J. Exp. Med.* 189:1723; Yu, B. et al. (2000) *Eur. J. Immunol.* 30:2497; and O'Shea, E. K et al. (supra)). These dimerization domains facilitate assembly of the soluble heterodimers and represent a functional replacement for the hydrophobic transmembrane regions that participate in the assembly of MHC class II molecules. The BirA biotinylation site (SEQ ID NO:6) was attached 3' to the Fos segment on the DRα chain construct (see, e.g., Beckett, D. et al. (supra)).

Because this method requires an abundant source of MHC/CLIP precursors in order to generate a series of tetramers, stable transfectants were created in CHO cells and grown at a high density in hollow fiber bioreactors. These reactors separate the cells from the bulk of the growth medium by a semi-permeable membrane that permits passage of nutrients but blocks diffusion of macromolecules secreted by the cells. Thus, secreted proteins are highly concentrated in the cellular compartment, allowing for the isolation of proteins produced by large numbers of cells from a small volume of growth medium. Affinity purification from these supernatants yielded abundant quantities of HLA-DR/CLIP precursors. From supernatants collected over one well from bioreactor cultures, the following quantities of HLA-DR/CLIP complexes were obtained: DR1—45.6 mg, DR2a—9.4 mg, DR2b—34.3 mg, and DR4—57.7 mg. The concentration of DR/CLIP complexes in bioreactor supernatants ranged from about 10.5 to 64 mg per 100 ml of supernatant, and was therefore much higher in the Baculovirus system (typically 1-2 mg per liter). Since these bioreactors were maintained for 2-3 months and 1 mg of DR/CLIP precursor was used per tetramer, a large number of different tetramers could be generated from this material and used for systematic analysis of $CD4^+$ T cell populations. Analysis by SDS-PAGE demonstrated that these preparations were pure, and confirmed specific cleavage of the linker by thrombin, which reduced the molecular weight of DRβ, but not DRα chain following cleavage (FIG. 1B).

Figure 2:
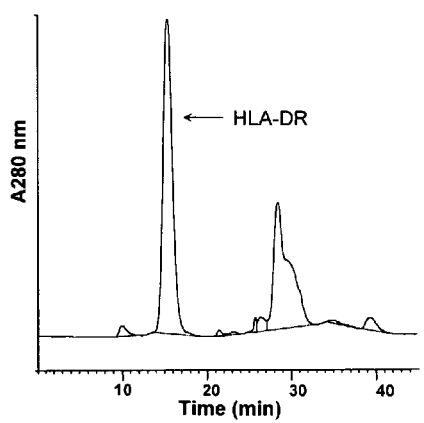
FIG. 2 illustrates the isolation of HLA-DR molecules loaded with a single peptide.
Figure 2:
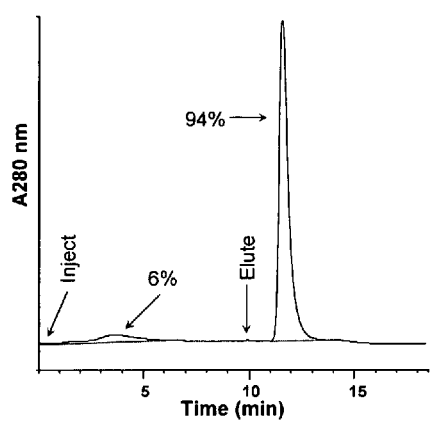
Figure 2:
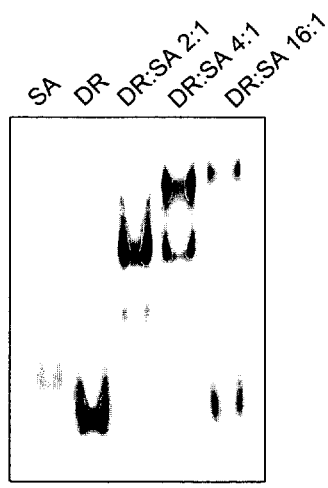

B. Kinetics of CLIP Dissociation and Peptide Association; Exchange of CLIP with Viral Peptides Due to the long half-life of bound peptides, the kinetics of peptide binding to HLA-DR molecules purified from antigen presenting cells is very slow. Thus, it was reasoned that DR molecules may be in a peptide-receiving state following dissociation of the CLIP peptide. Accordingly, the kinetics of CLIP dissociation and peptide association were evaluated using DR molecules (thrombin-cleaved) that were loaded with an Alexa-488 labeled CLIP peptide (SEQ ID NO:8) (FIGS. 1C and 1D). The DR/CLIP-Alex-488 complex was quantitated at different time points following addition of a large molar excess of unlabeled competitor peptide. The labeled DR/CLIP-Alex-488 complex was separated from unbound peptide by HPLC gel filtration chromatography and measured with a fluorescence detector, with the surface area of the peak corresponding to the amount of bound fluorescent peptide (FIG. 2A). The experiments demonstrated a rapid dissociation of the fluorescent CLIP peptide from DR4 at an acidic pH (pH 5.2). Due to the short $t_{1/2}$ of 5.3 minutes, almost all of the bound CLIP peptide had dissociated within 30 minutes (FIG. 1C). Association of an Alexa-488 labeled influenza HA (amino acids 306-318; SEQ ID NO:9) peptide was examined using the same approach. The kinetics of peptide association closely mirrored those observed for CLIP dissociation, with a $t_{1/2}$ of 5.4 minutes (FIG. 1D). The kinetics of CLIP dissociation and peptide association could be further accelerated by the addition of HLA-DM ($t_{1/2}$ of 2.5 minutes for binding of the HA peptide) (FIG. 1D).

Since the CLIP peptide binds to all human and murine MHC class II molecules and the polymorphic residues in the MHC class II binding site determine the kinetics of CLIP dissociation and peptide association, the kinetics of CLIP dissociation and peptide association for DR2a (DRB5*0101) were also evaluated. CLIP dissociation from this DR molecule was slower, with a $t_{1/2}$ of 3-4 hours. Again, the rate of peptide association mirrored the rate of CLIP dissociation.

These experiments demonstrated that DR molecules are in a peptide-receptive state following CLIP dissociation, and that CLIP dissociation determines the rate of peptide binding. Thus, due to the presence of the CLIP peptide during biosynthesis and purification, DR molecules do not enter a peptide-averse state, in which they may be partially denatured. Furthermore, the expression of DR molecules as precursors with a bound CLIP peptide greatly increased their biological activity, as shown by the rapid binding of peptides following CLIP dissociation.

C. Generation of Tetramers from DR/CLIP Presursors

Next, peptides were synthesized with an N-terminal affinity tag (dinitrophenol, DNP), which can be readily incorporated during synthesis and allows affinity purification of DR molecules loaded with the peptide of interest. DR molecules were first incubated with a molar excess of these DNP-labeled peptides, and two chromatography steps were employed to isolate defined DR/peptide complexes. DR/peptide complexes were first separated from free DNP-labeled peptide by HPLC gel filtration chromatography (FIG. 2A). Next, the DR/peptide fraction from the gel filtration separation was injected into a HPLC DNP-affinity column. This affinity purification step also allowed for the determination of the fraction of DR molecules from the HPLC gel filtration step that were loaded with the DNP-labeled peptide, based in the surface area of the peaks that represented bound and unbound protein (FIG. 2B). This loading efficiency ranged from 53% to approximately 100% for a variety of different peptides. The DNP-affinity purification therefore confirmed loading of the peptide of interest and provided a homogenous DR/peptide preparation even for peptides that were not loaded at a high efficiency (FIG. 2C).

D. Specificity of Tetramer Staining

Figure 3A:
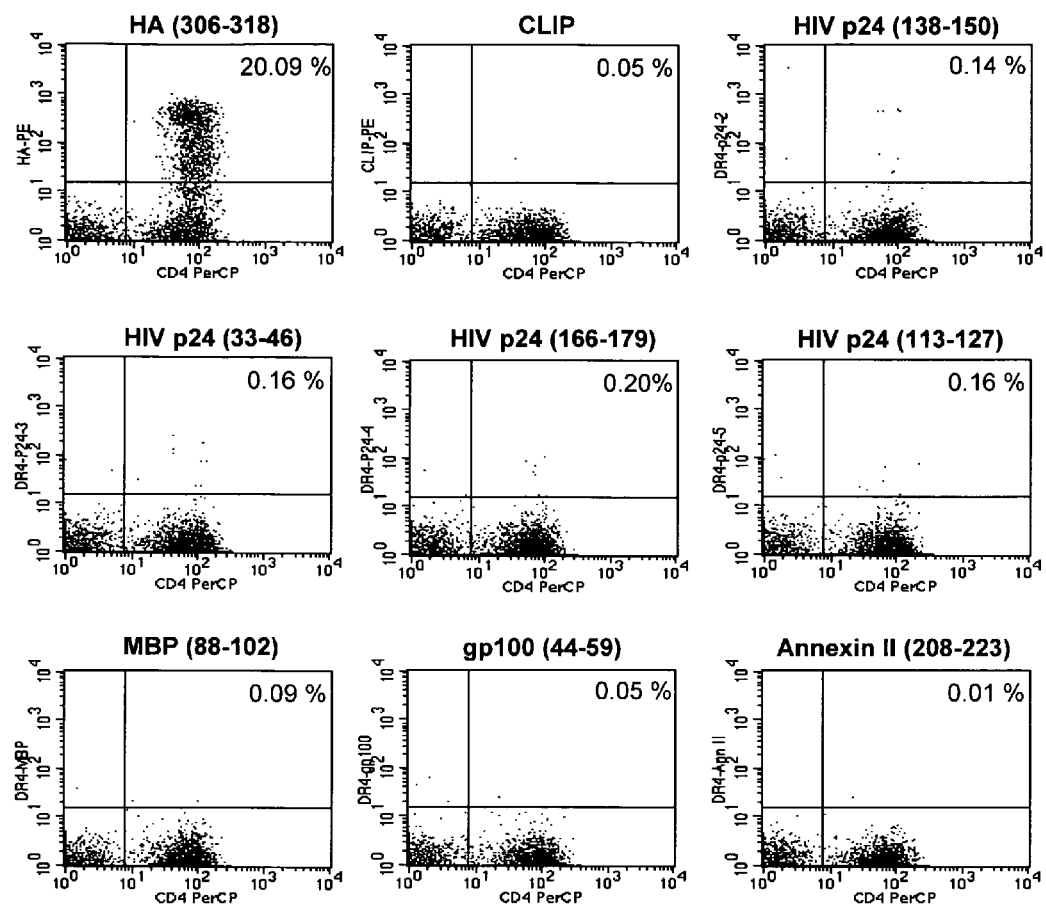
FIGS. 3A-3C are flow cytometry (FACS) analyses of influenza HA specific T cell lines showing the specificity of tetramer staining in subjects with different DR haplotypes.
Figure 3B:
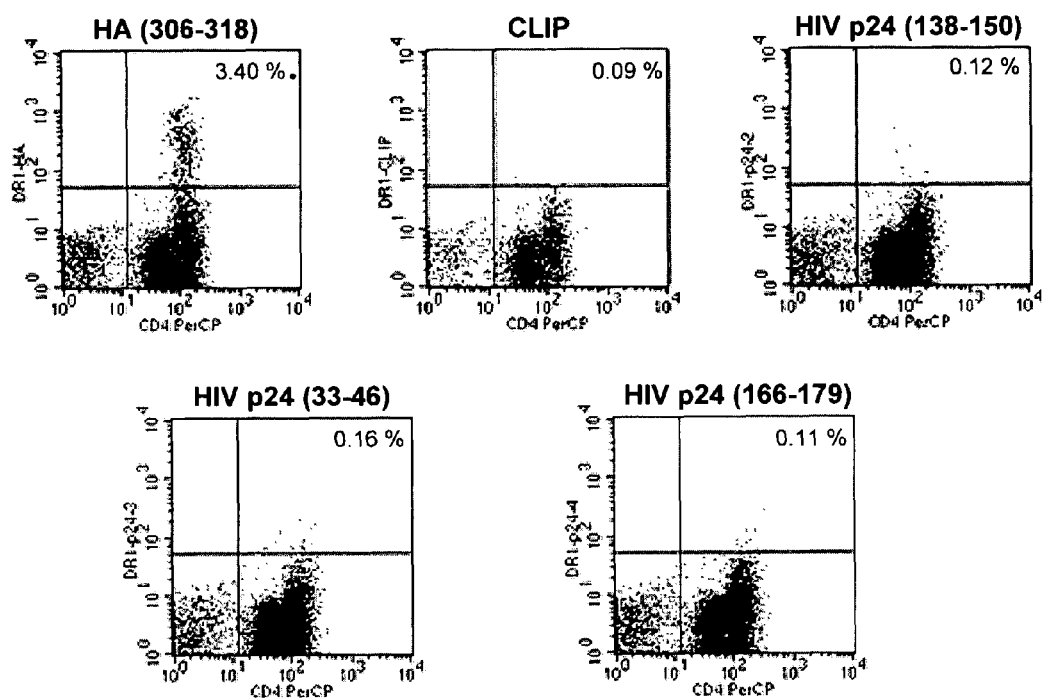
Figure 3C:
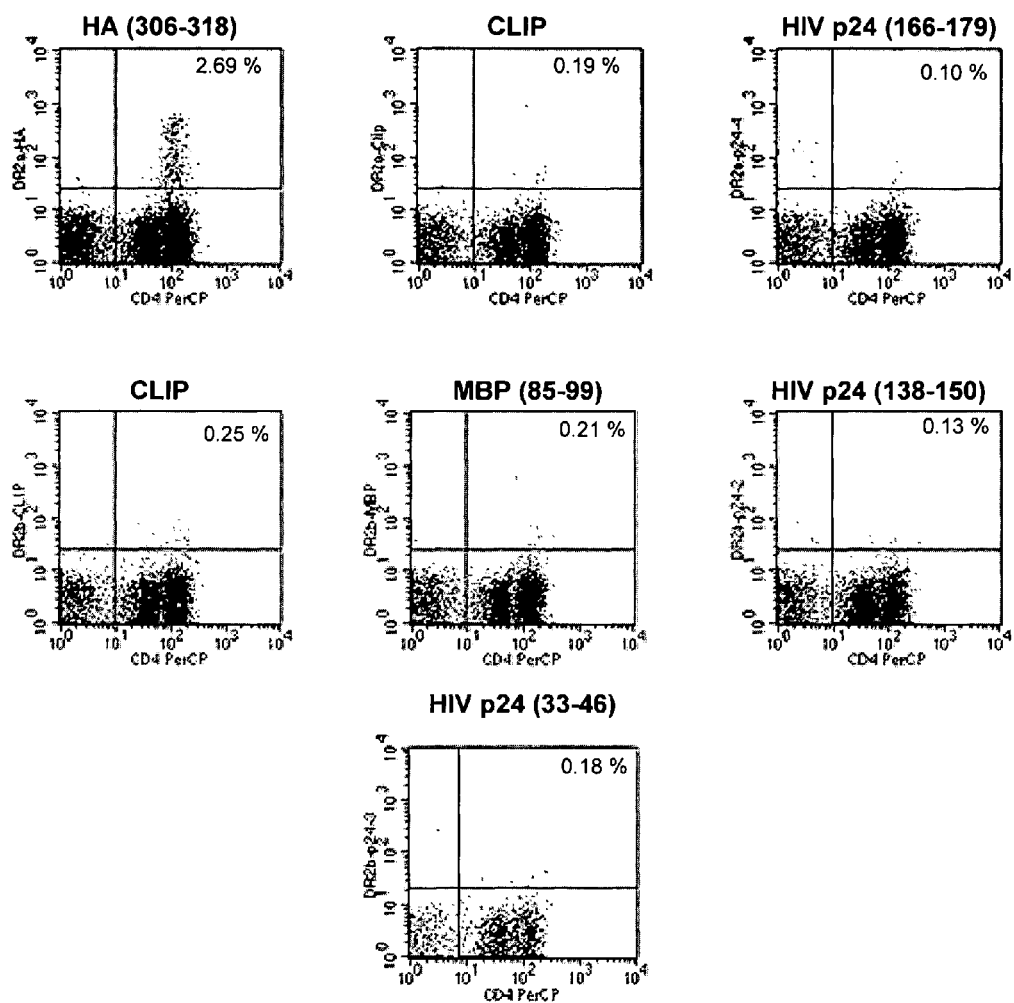

Short term T cell lines were generated from blood mononuclear cells of a normal donor with the DRB1*0401 haplotype by stimulation with the influenza HA (amino acids 306-318) peptide (see, e.g., Eckels, D. D. et al. (1984) *Immunogenetics* 19:409). T cells specific for the DR4-HA peptide complex could be readily visualized at day 7 following initiation of cultures, with 3.59% of CD4$^+$ T cells staining with the DR4-HA tetramer compared to 0.01% with the DR4-CLIP control. All tetramer-positive wells expressed high levels of the CD25 activation marker. To establish the specificity of tetramer staining, a panel of eight (8) control tetramers that had been loaded with other DRB1*0401 binding sites was used. These control peptides included CLIP (SEQ ID NO:1), a myelin basic protein peptide (amino acids 88-102; SEQ ID NO:18), the gp100 peptide (amino acids 44-59; SEQ ID NO:16) and annexin II peptide (amino acids 208-223; SEQ ID NO:17) which had been eluted from melanoma cells, as well as four (4) peptides from HIV p24 (SEQ ID NOs:10, 12-14) (see below and also, e.g, Valli, A. et al. (1993) *J. Clin. Invest.* 91:616 and Halder, T. et al. (1997) *Cancer Res.* 57:3238). These experiments demonstrated bright staining with the DR4/HA tetramer, but none of the eight control tetramers (FIGS. 3A-3C). An influenza HA (amino acids 306-318; SEQ ID NO:9) specific T cell line was also established from a normal donor with the DR2 haplotype, and a specific staining was observed with a DR2a/HA tetramer (DRB5*0101).

Figure 4:
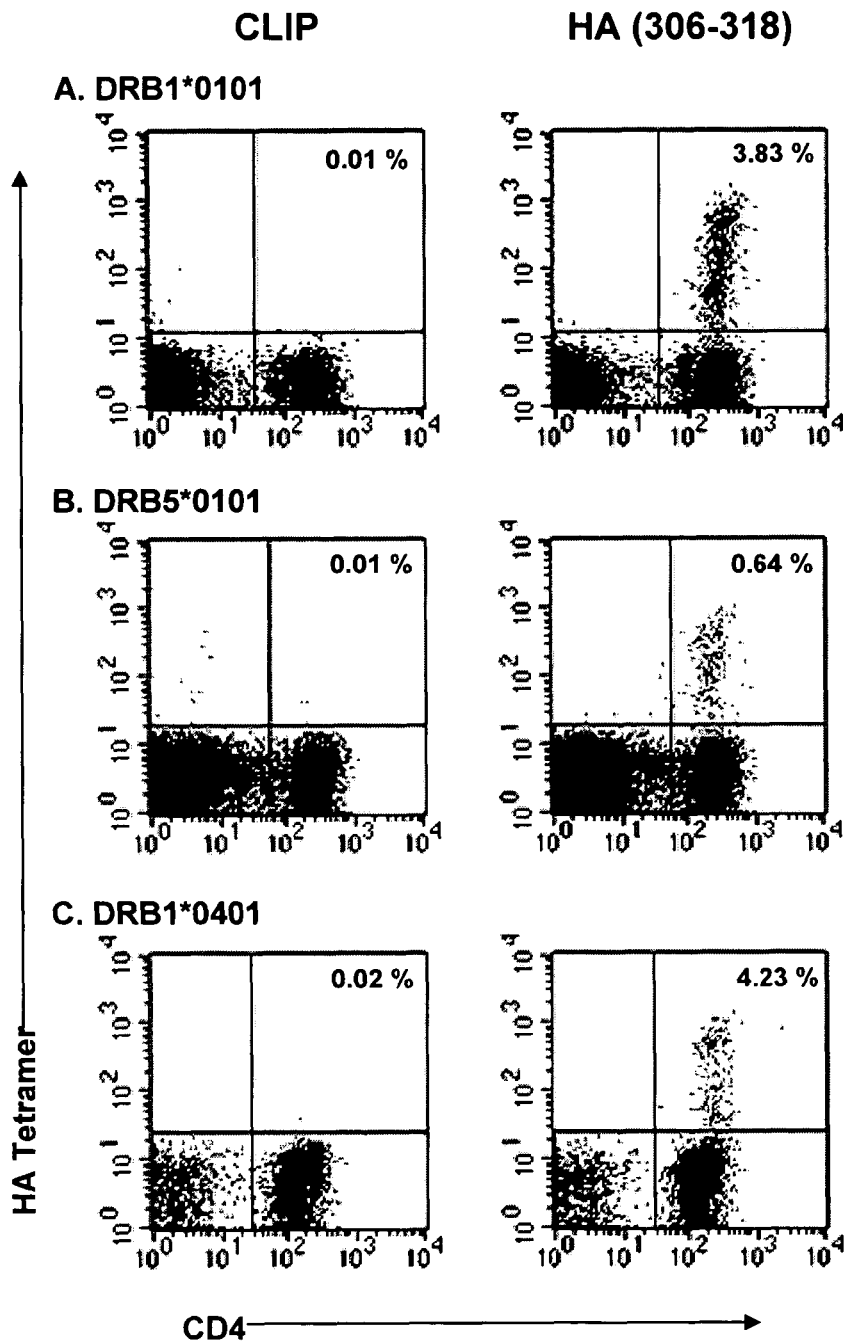
FIG. 4A-4C is FACS analysis showing the specificity of tetramer staining in short-term influenza HA-specific T cell lines from three different subjects.
Figure 5:
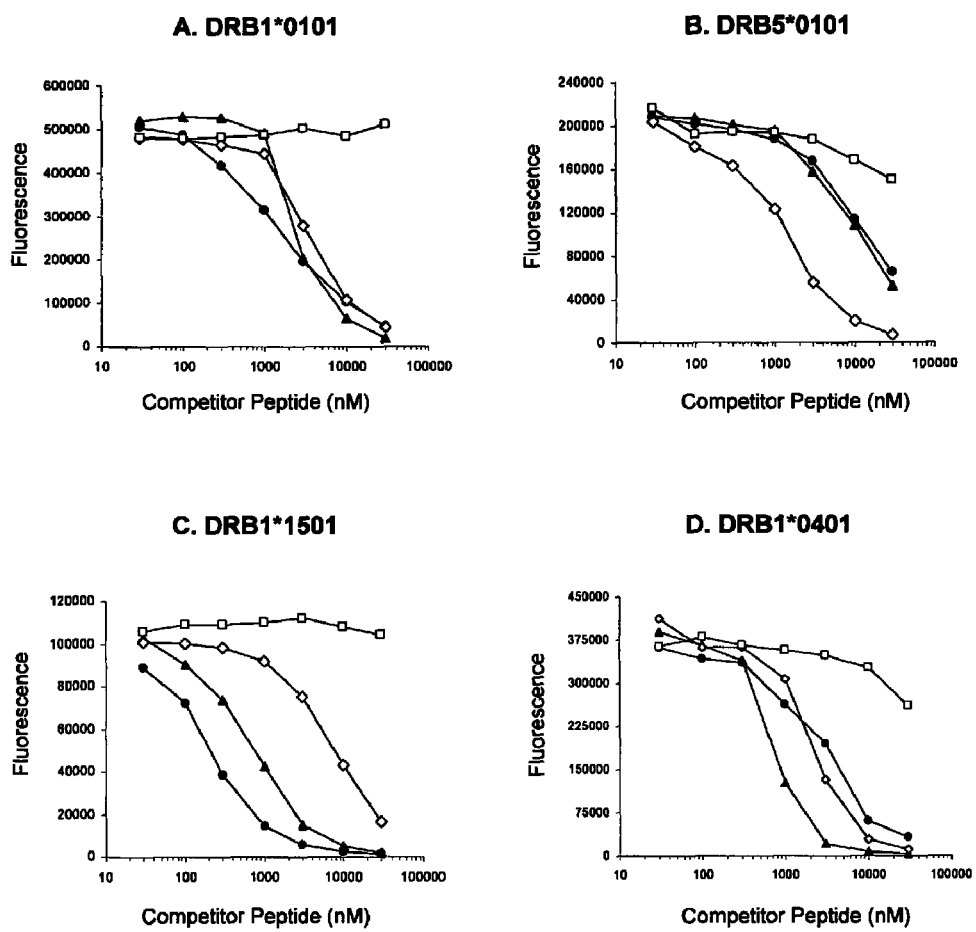
FIGS. 5A-5D illustrate the identification of HIV p24 peptides associated with different MHC molecules in competition assays.

Since the influenza HA (306-318) peptide binds to three of the four DR molecules that were expressed (Denzin, L. K., and Cresswell, P. (1995) *Cell* 82:155; Hammer, J., et al. (1993) *Cell* 74:197), short-term T cell lines were generated from normal donors with the DRB1*0101, DRB1*0401 or DRB1*1501 haplotypes. The corresponding tetramers labeled distinct populations of CD4$^+$ T cells in these lines (FIG. 4) indicating that tetramers generated by this approach were functional and specifically label antigen-specific human CD4$^+$ T cells.

E. Identification of HIV p24 Peptides that Bind to Multiple HLA-DR Molecules

Next, the tetramers of the present invention were evaluated to determine if they could be used to directly visualize virus-specific T cells from peripheral blood without prior in vitro expansion. Analysis of HIV-specific CD4$^+$ T cells with MHC class II tetramers could be of particular interest to those skilled in the art since proliferative responses to the HIV p24 antigen are detected during the acute stage of the disease, but are weak or absent during the chronic progressive stage (see, e.g., Rosenberg, E. S. (1997) *Science* 278:1447). Since staining with tetramers does not depend on particular T cell functions, such as proliferation or γ-interferon production, tetramers may be useful in determining the fate of HIV-specific CD4$^+$ T cells during the course of disease (i.e., the loss of particular functions or deletion).

Because only a limited number of CD4$^+$ T cell populations to the relevant antigen(s) may be highly expanded, generation of the most useful tetramers requires careful selection of candidate peptides. Previous studies demonstrated that the HIV p24 antigen is a major target for CD4$^+$ T cells. Accordingly, an overlapping set of peptides from the HIV p24 antigen was evaluated in peptide binding and T cell assays. Peptide binding was examined in competition assays using all four allelic forms of HLA-DR molecules that had been expressed. Three of the 23 peptides (HIV p24 amino acids 31-52, 131-152 and 161-182; SEQ ID NOs:10, 12-14) bound to all four DR molecules that were tested, with IC$_{50}$ values ranging from 0.22 µM to 10.5 µM (see Table I and FIGS. 5A-5D). By comparison, IC$_{50}$ values of 0.22 µM to 0.55 µM were determined for the high affinity peptides from influenza HA (amino acids 306-318; SEQ ID NO:9) and MBP (amino acids 85-99; SEQ ID NO:18) peptides that were used as a positive control (FIGS. 5A-5D). Three other peptides bound to two or of the four DR molecules that were studied (see Table 1).

Interestingly, T cell assays demonstrated that three of the peptides identified in the binding studies are immunodominant targets of the CD4$^+$ T cell response to HIV p24 in patients with the relevant HLA-DR haplotypes. Proliferative responses to these peptides were also observed in some patients with other HLA-DR haplotypes, indicating that other MHC class II molecules can also present these peptides.

F. Direct Ex Vivo Identification of HIV-Specific CD4$^+$ T Cells

Figure 6:
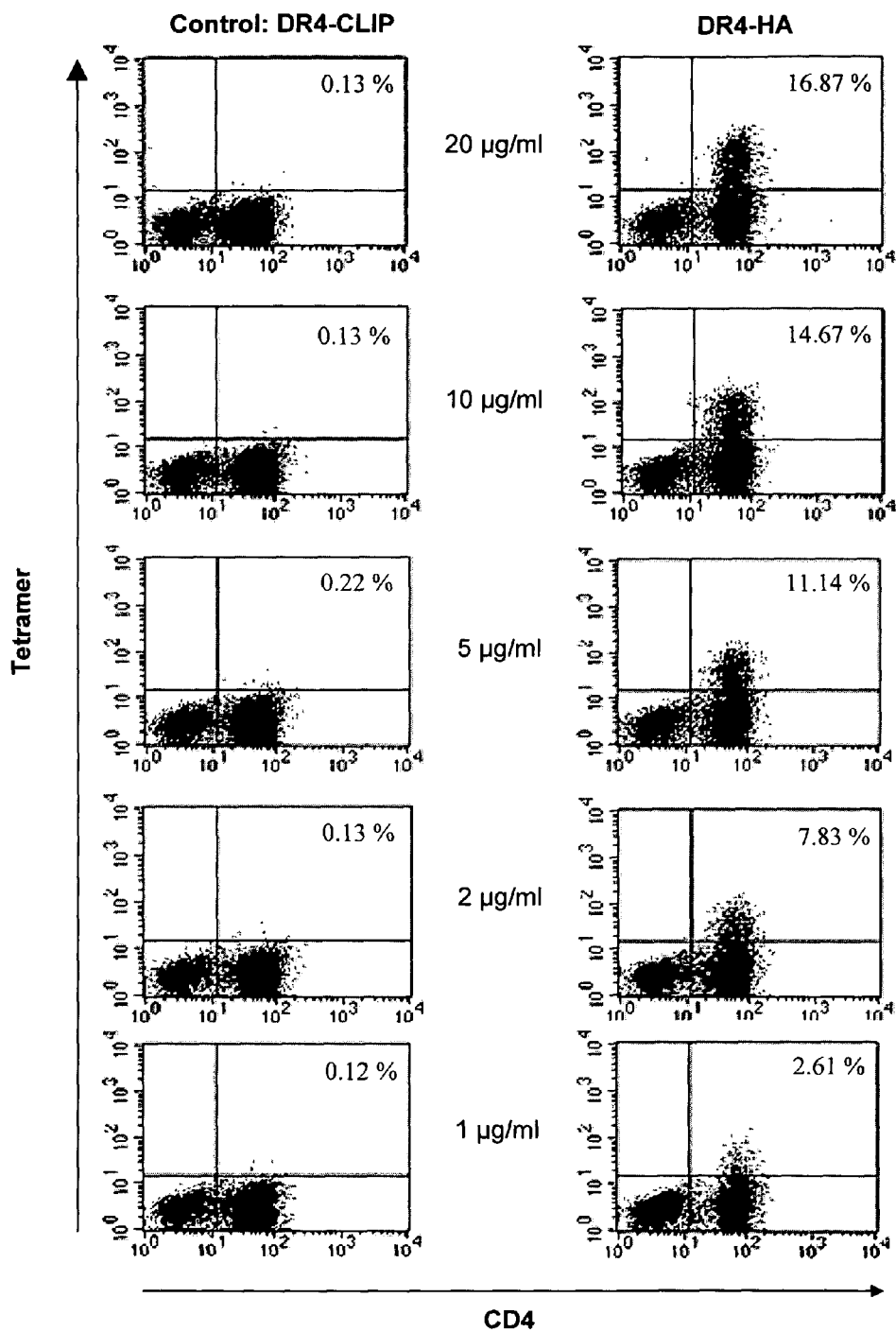
FIG. 6 is FACS analyses illustrating the dose-dependent staining of influenza HA-specific T cells.
Figure 7:
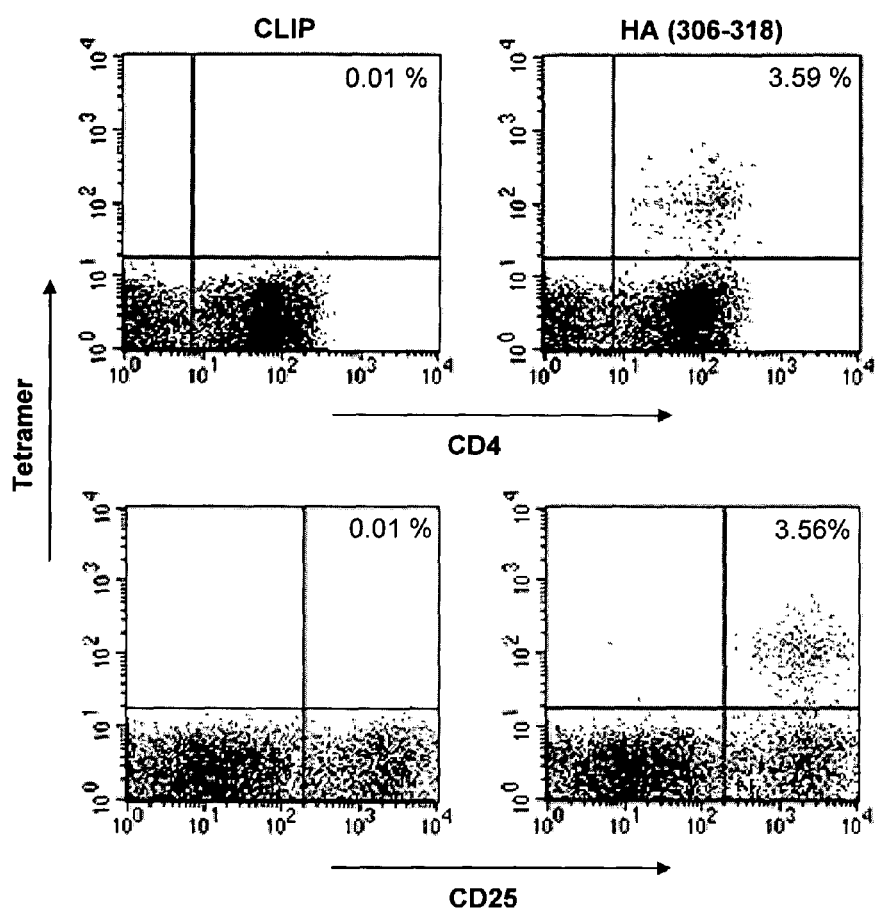
FIG. 7 is FACS analyses illustrating the association of DR4 tetramers with the influenza HA peptide on activated, CD25$^+$ T cells.

The direct ex vivo identification of T cells was assessed by 4-color FACS analysis in HIV-infected patients that had been treated with anti-retroviral therapy during the acute stage of infection. Isolated, purified CD4$^+$ T cells from peripheral blood were stained for two hours with 20 µg/ml tetramers followed by the addition of labeled antibodies (tetramer-PE, annexin V-Alexa-488, CD3-APC and CD4-PerCP) during the last half hour of incubation. For controls, the DR/CLIP complex as well as two naturally processed peptides that bound to DR4 with high affinity [gp100 (amino acids 44-59) (SEQ ID NO:16) and annexin II (amino acids 208-223) (SEQ ID NO:17)] were used. Following washing, the cells were stained with annexin V, to permit the exclusion of apoptotic cells, and measured by FACS analysis. The cells were gated based on forward scatter/side scatter, as well as expression of CD3 and CD4 (see, e.g, FIGS. 6 and 7).

These experiments demonstrated a marked expansion of HIV-specific CD4$^+$ T cells in these HIV infected patients. Specifically, three of the tetramers identified expanded p24-specific T cell populations in all three patients, with frequencies ranging from 0.22 to 1.62% (Table 2). Initial analysis with the fourth peptide (amino acids 138-150; SEQ ID NO:13) did not demonstrate a significant population of cells. However, analysis of the p24 sequences of different viral strains demonstrated that many viral isolates have a threonine to valine substitution at position 148, a likely TCR contact residue (P8 position). Thus, a tetramer was generated containing this variant peptide (138-150V). This tetramer labeled a distinct population in one of two patients, but not in a HLA-mismatched subject (Table 2). Therefore, all four HIV p24 tetramers identified expanded populations of CD4+ T cells. No significant labeling was observed in two seronegative subjects with the appropriate MHC allele (DRB1*0401), or in an MHC mismatched, HIV infected patient. These results demonstrate for the first time that antigen-specific CD4+ T cells can be directly identified ex vivo in a human disease from peripheral blood.

2. Example 2

This example further illustrates the development of MHC class II tetramers that are based on the cellular peptide loading mechanism of the present invention. The results show that peptides from the Hepatitis C virus (HCV) were identified that bound to multiple allelic forms of HLA-DR. These tetrameric forms of HLA-DR/HCV complexes were able to label expanded populations of low frequency human virus-specific memory CD4+ T cells directly ex vivo in patients who spontaneously resolved HCV viremia.

Materials and Methods

A. Subjects

Seven anti-HCV positive subjects (four HLA DRB1*0401-positive and three HLA DRB1*0401-negative) were included in this study. All subjects were anti-HCV positive as measured by enzyme immunoassay. HCV viral loads were measured by the Roche Amplicor Monitor assay (detection limit 300 copies/ml of plasma). Subjects 98A and 01-40 spontaneously resolved HCV viremia, and subject 99D was treated with IFN/ribavirin therapy and subsequently resolved HCV viremia; all three subjects had persistent documented undetectable plasma viral loads (<300 copies/ml of plasma). Based on RT-PCR analysis, the infection had been resolved for the following time periods in these subjects: 98A>4.5 years, 01-40: >4 months; 99D:>3.5 years. Subject 99-24 had chronic HCV viremia (viral load 38,600 copies/ml of plasma). HLA typing was performed by standard serological and molecular techniques (Bunce, M., et al. (1995) *Tissue Antigens* 46:355). The HLA class II DR alleles of the HLA DRB1*0401-positive subjects included in this study are as follows: 98A: DRB1*0401, DR*10; 01-40: DRB1*0401, DRB1*07, 99D: DRB1*0401; 99-24: DRB1*0401, DRB1*15.

B. Expression of DR/CLIP Precursors

The constructs for the expression of DR/CLIP complexes were prepared as described above in Example 1A.

C. Processing of DR Molecules: Biotinylation Thrombin Cleavage, and Peptide Exchange Purified DR molecules were biotinylated and cleaved with thrombin as described above in Example 1B.

Peptide exchange was performed using dinitrophenol-labeled peptides for affinity purification of defined DR/peptide complexes. The dinitrophenol group was attached to the N-terminus of peptides via an aminohexanoic acid (Ahx) linker during synthesis (New England Peptide, Fitchburg Mass.); all peptides were HPLC purified and analyzed by mass spectrometry. The sequences of the HCV peptides used for construction of MHC class II tetramers were as follows: HCV 1248: GYKVLVLNPSVAATL (SEQ ID NO:19); HCV 1579: SGENLPYLVAYQATVCARA (SEQ ID NO:20); HCV 1770: SGIQYLAGLSTLPGNPAIASL (SEQ ID NO:21). Control tetramers were generated with peptides that had been eluted from DR4 molecules expressed by a melanoma cell line, annexin II (res. 208-223): DVPK-WISIMTERSVPH (SEQ ID NO:17); and gp100 (res. 44-59): WNRQLYPEWTEAQRLD (SEQ ID NO:16) (Halder, T., et al. (1997) *Cancer Res.* 57:3238).

Peptide exchange reactions were carried out with 3.3 µM *DR/CLIP and 50 µM of the respective DNP-labeled peptide in a buffer containing 50 mM sodium citrate pH 5.2, 1% octylglucoside, 100 mM NaCl, 1× protease inhibitor cocktail (Sigma). The reactions were incubated overnight at 30° C. and then concentrated by ultrafiltration. The *DR/CLIP concentration and reaction temperature were chosen based on preliminary experiments designed to minimize aggregation of empty DR molecules created by CLIP dissociation. Aggregation was substantially lower at *DR/CLIP concentrations of 3.3 µM compared to 8.25 µM, and at a reaction temperature of 30° C. rather than 37° C. DR molecules were separated from unbound peptide using a Superose 12 HPLC gel filtration column (Amersham Pharmacia Biotech, Piscataway N.J.) using PBS at a flow rate of 0.8 ml/min. The peak representing DR molecules was collected and injected onto an anti-DNP HPLC affinity column. The anti-DNP affinity column was generated by covalently cross-linking 10 mg of anti-DNP-1 antibody (Biotrend Chemikalien, Cologne, Germany) to a 4.6 mm×50 mm protein G column on POROS 20 XL media (Applied Biosystems, Foster City Calif.). DR molecules with bound DNP-peptide were eluted from the column using 50 mM CAPS [3-(Cyclohexylamino)-1-propanesulfonic acid] pH 11.5 and eluates were neutralized by addition of 1 M phosphate, pH 6.0. Biotinylated, peptide loaded DR molecules were concentrated by ultrafiltration (Centrion 2 ml concentrator, Millipore, Bedford Mass.) and the buffer was simultaneously changed to PBS. Biotinylated DR/peptide complexes were frozen in small aliquots at −80° C. and multimerized with labeled streptavidin prior to use in staining reactions.

D. Peptide Binding Assay

Competition assays were performed to identify HCV peptides suitable for tetramer production. HCV peptides were used as competitors for binding of a biotinylated influenza HA (306-318) peptide (SEQ ID NO:9) to thrombin-cleaved DR4/CLIP complexes. Competitor peptides were tested at concentrations ranging from 30 nM to 10 µM in the presence of 30 nM of labeled HA peptide and DR/CLIP at 1.7 µM. Reactions were incubated for 20 hours at 37° C. in 50 mM sodium citrate pH 5.2, 1% octylglucoside, 100 mM NaCl, 100 µg/ml of BSA, 1× protease inhibitor cocktail. 100 ng of DR was loaded onto a 96 well plate (Wallac, Oy, Finland) coated with 200 ng/well of mAb L243 and DR-bound peptide was detected with europium-labeled strepavidin. Fluorescence was quantitated using a Delfia 1234 fluorometer (Wallac).

E. Generation of HCV-Specific CD4+ T Cell Lines

HCV-specific CD4+-T cell lines were generated as previously described (Day, C. L., et al. (2002) *J. Virol.* 76:12584).

F. Labeling of T Cells With MHC Class II Tetramers

For HCV tetramer formation, biotinylated DR/peptide complexes were incubated with R-phycoerythrin-labeled streptavidin for at least one hour on ice, at a 4:1 molar ratio of DR to streptavidin and a final DR concentration of 0.2 mg/ml. Cells (either fresh PBMC, cryopreserved PBMC, or cells from a short-term stimulated line) were stained in 100 µl R10 medium (RPMI, 10% fetal calf serum, 10 mM HEPES, 2 mM L-glutamine, 50 U/ml Penicillin-Streptomycin) with 2 µg of PE-conjugated MHC class II tetramer for 2 hours at room temperature. APC-conjugated anti-CD4+, PerCP-conjugated anti-CD14, PerCP-conjugated anti-CD19, and either FITC-conjugated CD27 or CD4+5RA MAbs were added for the last 20 minutes of incubation. For CCR7 analysis, cells were stained with unconjugated anti-human CCR7 antibody (Becton Dickinson) during the last 20 minutes of tetramer incubation, then washed twice and stained with a secondary anti-mouse-IgM-FITC-conjugated antibody. The cells were incubated for 20 minutes and washed twice, and then anti-CD4, CD14, and CD19 were added and the cells incubated for an additional 20 minutes. Cells were washed twice and then stained with anti-PE MicroBeads (Miltenyi Biotec, Auburn, Calif.) for 20 minutes at 4° C. The cells were washed once and 90% of the cells were applied to MS separator columns (Miltenyi Biotec, Auburn, Calif.) according to manufacturer's instructions. The other 10% of the tetramer stained cells were reserved for FACS analysis; the total number of cells in this pre-enrichment sample was multiplied by 10 to determine the input number of cells for each sample. Two to three million PBMC were used for each tetramer stain. The PE-positive cells were then eluted from the columns, stained with Via-Probe (Becton Dickinson), and analyzed by flow cytometry using CellQuest software. Cells were gated on CD4+, CD14−, CD19−, and Via-Probe− cells. Multiple control tetramers with irrelevant peptides were used in most experiments to demonstrate specificity of binding by the relevant tetramers. The frequency of tetramer+ cells was determined by dividing the number of CD4+/tetramer+ cells after enrichment by the total number of CD4+ T cells as calculated by FACS analysis of the pre-enrichment sample. For Vβ analysis, cells were labeled with FITC-conjugated antibodies (Immunotech, Westbrook, Me.) following magnetic enrichment and washed following a 20-minute incubation at room temperature.

G. Intracellular Cytokine Staining

Intracellular cytokine staining of PBMC ex vivo and in short-term stimulated cell lines was performed as previously described (Day, C. L., et al. (2002) *J. Virol.* 76:12584).

Results

A. Identification of HCV Peptides that Bind to Multiple HLA-DR Molecules

Figure 8:
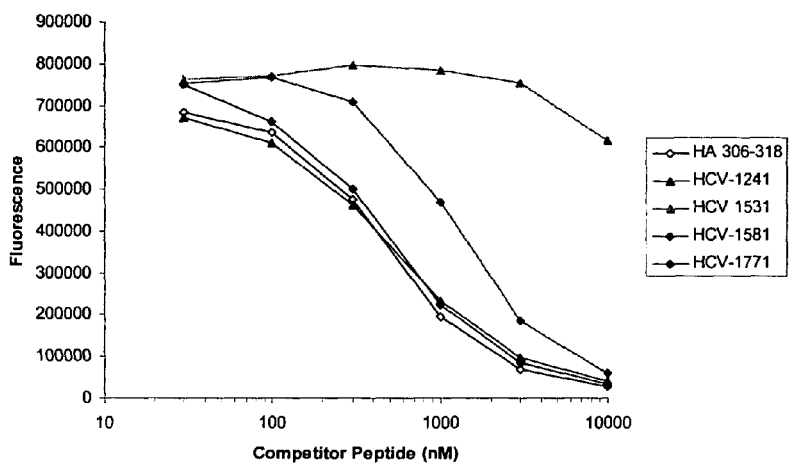
FIG. 8A illustrates the identification of HCV peptides associated with DR4 molecules in competition assays.
FIGS. 8B-8C show the isolation of DR4 molecules loaded with HCV peptides by gel filtration and affinity chromatography.
Figure 8:
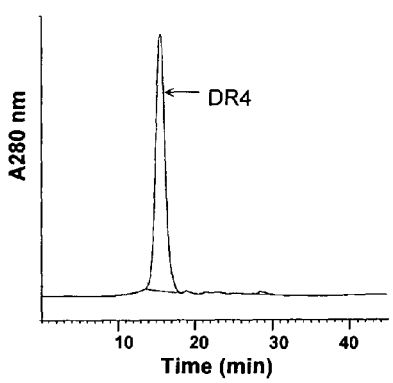
Figure 8:
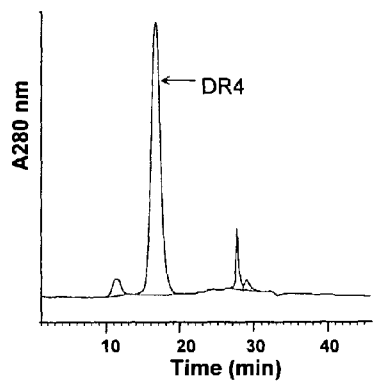
Figure 8:
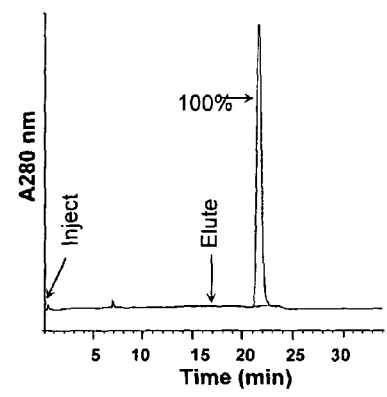
Figure 8:
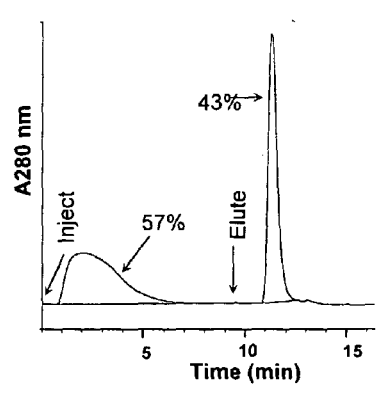

The materials and methods of the present invention were successfully applied to assess a clinically relevant chronic viral disease, Hepatitis C virus (HCV) infection. Since the MHC restriction elements are difficult to determine for polyclonal human CD4+ T cell populations, DR4 (DRA, DRB1*0401) binding of seven HCV peptides were examined. These DR4 epitopes are those that represent broadly recognized T cell epitopes for which the restricting class II alleles had not been unequivocally defined (Day, C. L., et al. (2002) *J. Virol.* 76:12584; Diepolder, H. M., et al. (1997). *J. Virol.* 71:6011). Three HCV peptides bound to DR4 (aa 1241-1260 (SEQ ID NO:19), aa 1581-1600 (SEQ ID NO:20), and aa 1771-1790 (SEQ ID NO:21)) and two of these competed for binding of labeled peptide as effectively as the influenza HA (306-318; SEQ ID NO:9) peptide and represents one of the highest affinity DR4 binders (FIG. 8A) (Denzin, L. K., and Cresswell, P. (1995) *Cell* 82:155; Hammer, J., et al. (1993) *Cell* 74:197). Based on the DRB1*0401 binding motif, peptides were chosen for synthesis in which the core nine-amino acid segment was flanked by several N- and C-terminal residues, and an affinity tag (dinitrophenol, DNP) was added to the N-terminus of each peptide. A two-step purification process was used to isolate complexes loaded with a single peptide. DR/peptide complexes were first separated from free DNP-labeled peptide by HPLC gel filtration chromatography (FIG. 8B), and the DR/peptide fraction from the gel filtration column was then injected into a HPLC DNP-affinity column (FIG. 8C). For the two high affinity HCV peptides, close to 100% of DR molecules injected into the DNP column carried the DNP-labeled peptide, while a smaller fraction (43%) was loaded for the lower affinity epitope. This affinity purification step therefore provided a homogenous DR/peptide preparation even for peptides that were not loaded with a high efficiency, an aspect that is relevant for the valency of the resulting staining reagents.

B. Direct Ex Vivo Identification of HCV-Specific Cd4+ T Cells

Figure 9:
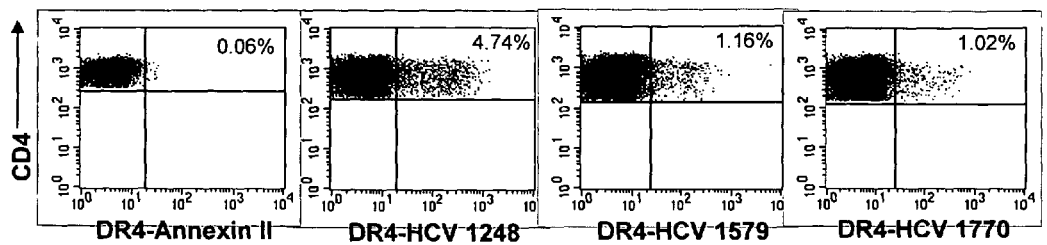
FIGS. 9A-9B are FACS analyses demonstrating the functionality of HCV tetramers, as well as enrichment of tetramer-labeled cells with anti-PE microbeads.
FIG. 9C is a FACS analysis of CD4$^+$/tetramer$^+$ cells illustrating effector function of HCV-specific T cells.
Figure 9:
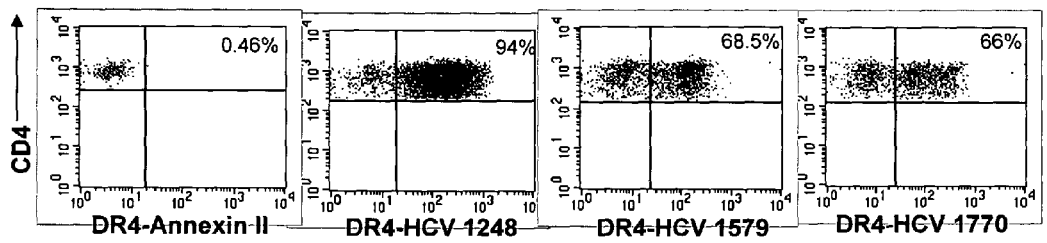
Figure 9:
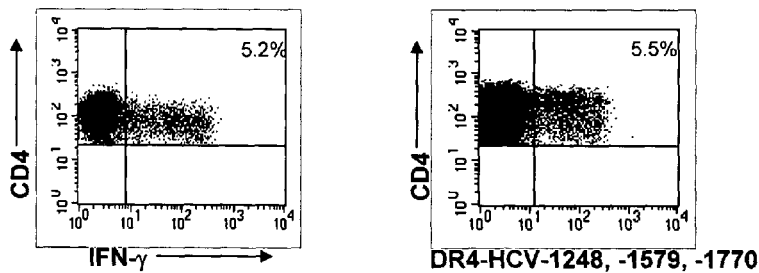

Each of the three DR4-HCV tetramers labeled a discrete population of CD4±T cells in short-term T cell lines generated from DRB1*0401-positive, anti-HCV-positive subjects by in vitro stimulation of peripheral blood mononuclear cells (PBMC) with soluble HCV NS3 and NS4 proteins, while no significant staining was observed with three control tetramers (DR4-Annexin II, DR4-gp100 and DR4-CLIP) (FIG. 9A). A substantial enrichment of labeled cells was obtained when anti-PE magnetic microbeads were used to capture cells stained with tetramers composed of DR4-HCV peptide complexes and streptavidin-PE. The CD4±/tetramer+ cells displayed effector function, as shown by parallel intracellular cytokine staining for IFN-γ and tetramer staining in an HCV NS3/NS4-stimulated line from subject 98A. A pool of the three HCV tetramers (DR4-HCV 1248, DR4-HCV 1579, and DR4-HCV 1770) stained approximately 5% of CD4±T cells from this line, consistent with 5% CD4/IFN-γ+ cells upon stimulation with a pool of the three HCV peptides corresponding to the tetramer epitopes (FIG. 9C).

Figure 10:
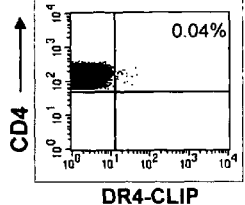
FIGS. 10A-10C are FACs analysis illustrating ex vivo MHC identification of HCV-specific CD4$^+$ T cells by magnetic enrichment with anti-PE microbeads.
Figure 10:
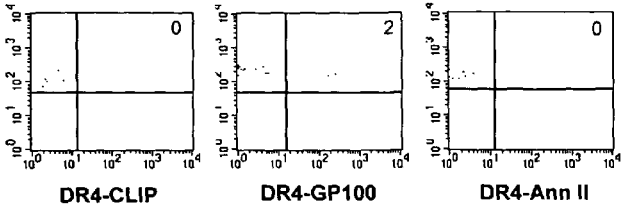
Figure 10:
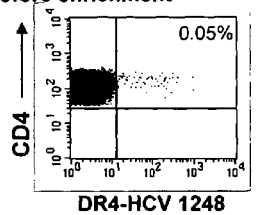
Figure 10:
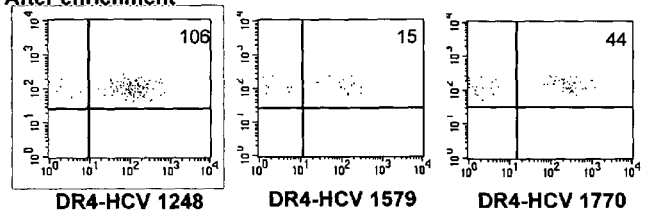
Figure 10:
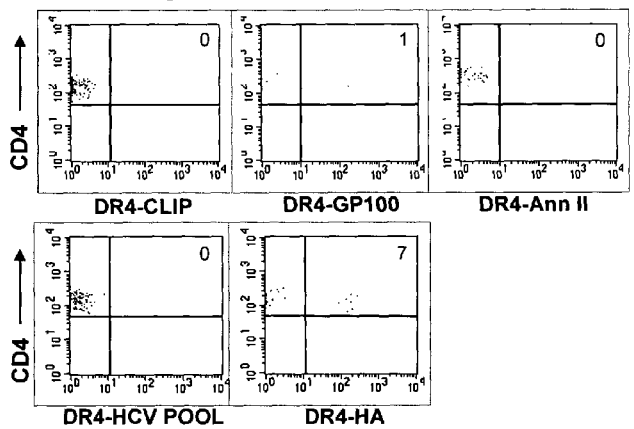
Figure 10:
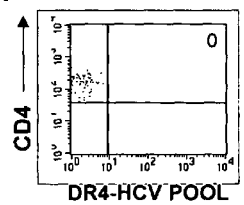

Tetramer-positive cells could not be unambiguously detected in fresh PBMC indicating that enrichment of labeled cells prior to FACS analysis might be essential. Fresh PBMC from subject 01-40, who spontaneously resolved HCV viremia, were stained with three control tetramers and three HCV tetramers, and tetramer-positive cells were then magnetically enriched with anti-PE microbeads. Following magnetic bead enrichment of cells labeled with control tetramers, 0-2 CD4+/tetramer+ cells were isolated, whereas discrete populations were identified for each of the three HCV tetramers with frequencies of 1 in 12,200 CD4± cells (0.008%) for DR4-HCV 1248, 1 in 66,000 (0.0015%) for DR4-HCV 1579, and 1 in 42,000 (0.0024%) for DR4-1770 (FIG. 10A). To ensure that the HCV tetramer-selected cells represented specific populations of CD4+ T cells, a similar analysis was performed on PBMC from a DRB1*0401-positive, HCV-seronegative donor (FIG. 10B). All three HCV DR4 tetramers were tested as a pool, and no CD4/tetramer+ cells were isolated in this seronegative control subject. A discrete population of cells was only observed with an influenza DR4-HA tetramer in this subject, and 7 CD4+/tetramer+ cells were isolated after enrichment (1 in 110,000; 0.0009%). Also, no staining with DR4-HCV tetramers was observed with PBMC from three MHC-mismatched (DRB1*0401 negative), HCV-infected control subjects.

In contrast to patients who spontaneously resolve infection with HCV, a CD4+ T cell response is difficult to detect in chronically infected subjects using assays based on particular effector functions (Day, C. L., et al. (2002) *J. Virol.* 76:12584), raising the question of whether HCV-specific CD4+ T cells are anergic or absent. PBMC from DRB1*0401+ subject 99-24 with chronic HCV were stained with a pool of all three HCV DR4 tetramers. No CD4+/tetramer+ cells were isolated from this patient, consistent with lack of a detectable response to these epitopes as measured by intracellular cytokine staining for IFN-γ production, response in proliferation assays, or ability to generate specific lines by culture with peptide and IL-2 (FIG. 10C).

C. Ex Vivo Phenotype of HCV-Specific CD4+ T Cells

Figure 11:
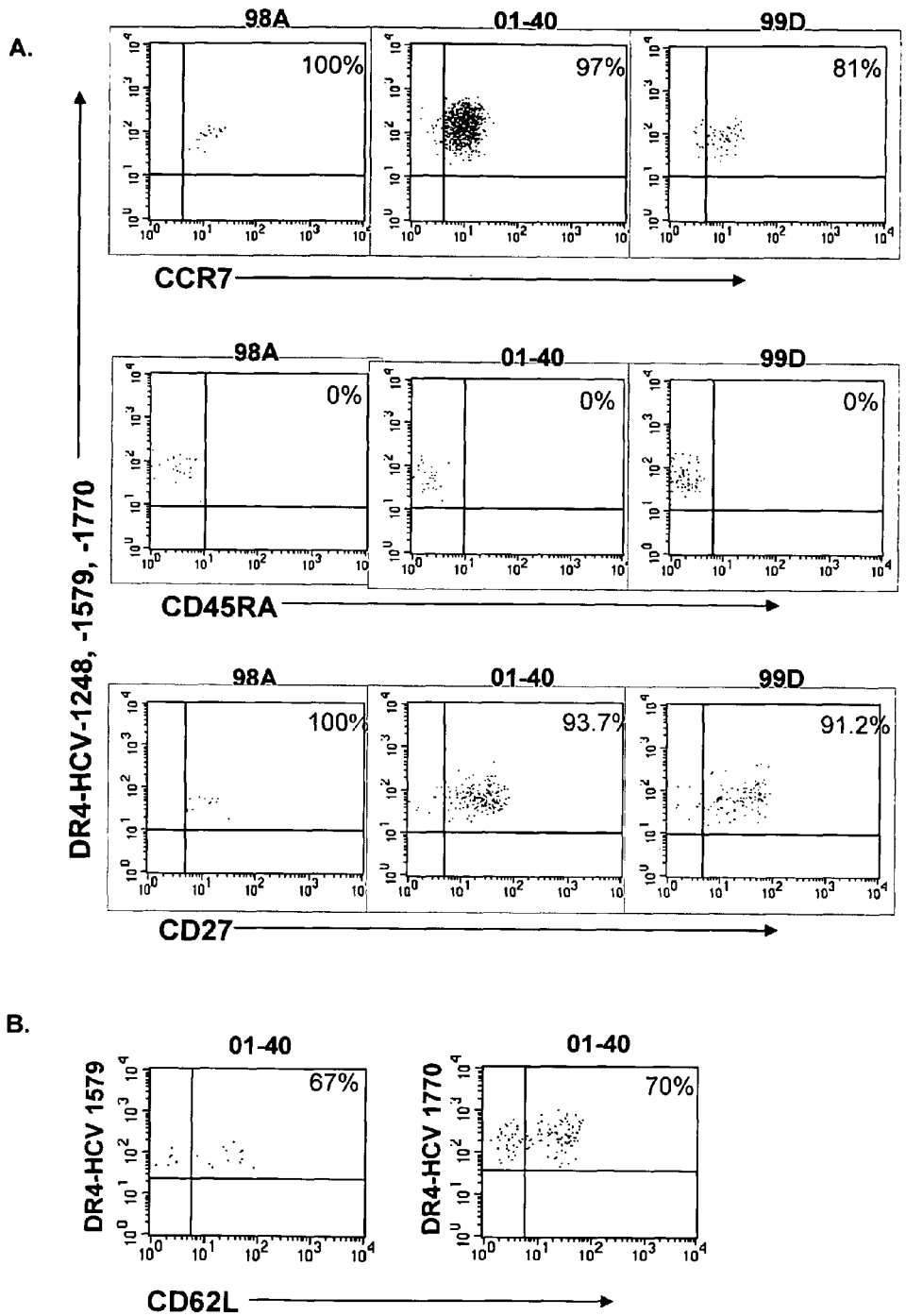
FIGS. 11A-11B are FACS analysis illustrating the identification of surface receptors important for memory T cell function of HCV specific T cells.

These data indicate that it is possible to study virus-specific CD4± T cells ex vivo, and therefore this approach was used to examine expression of surface receptors important for memory T cell function. The expression of the surface antigens CCR7, CD45RA, and CD27 on tetramer+ cells enriched from three DRB1*0401 subjects with resolved HCV viremia was examined. Isolated tetramer+ cells were CCR7+/CD27+/CD45RA−, consistent with a surveillance function for secondary lymphoid structures (FIG. 11A) (Sallusto, F., et al. (1999) Nature 401:708). The expression of the lymph node homing marker CD62L was analyzed on fresh PBMC from subject 01-40 in conjunction with the DR4-HCV 1579 and DR4-HCV 1770 tetramers, and 67% and 70% of CD4+/tetramer+ cells respectively were CD62L+ (FIG. 11B).

Figure 12:
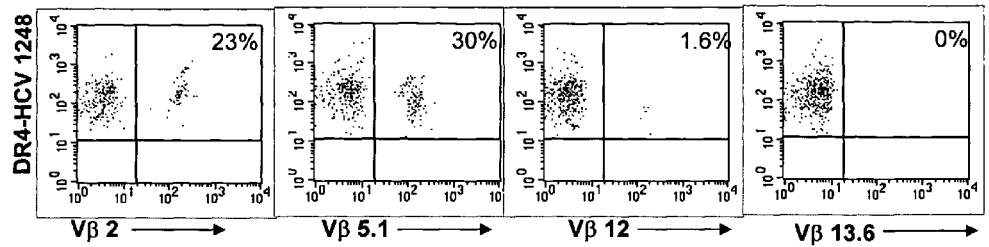
FIGS. 12A-12C are FACS analysis illustrating the TCR Vβ repertoire of HCV class II tetramer$^+$ cells.
Figure 12:
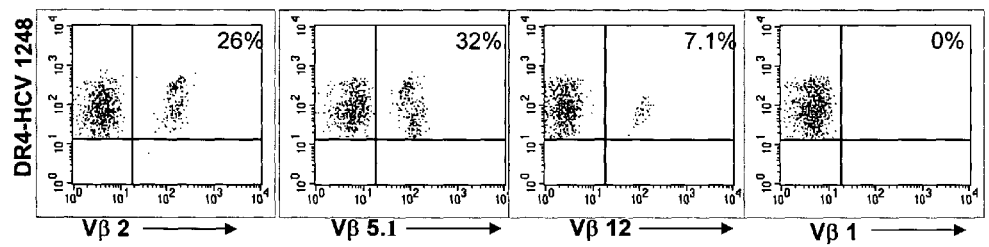
Figure 12:
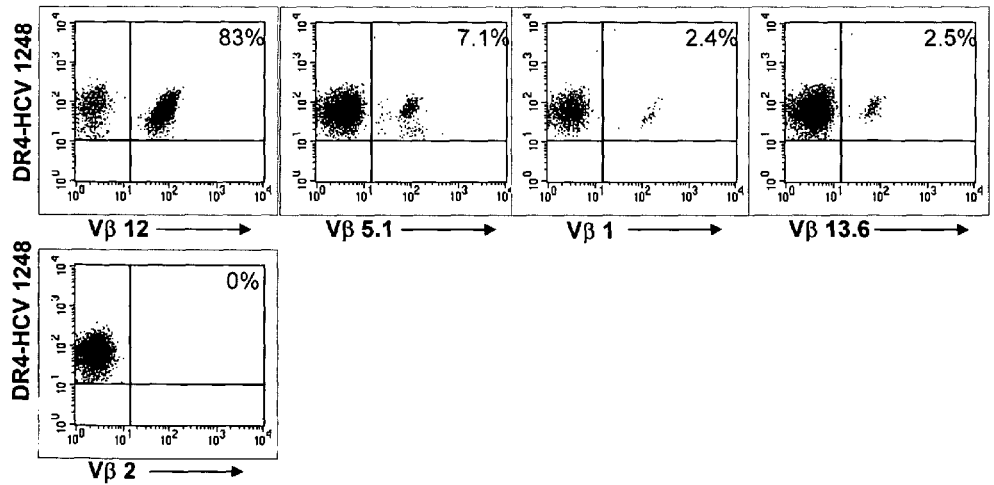

The HCV 1248 peptide has been described as an immunodominant CD4+ T cell epitope in HCV infection (H. M., et al. (1997) J. Virol. 71:6011), offering the possibility to determine the breadth of TCR usage by memory CD4+ cells in controlled HCV infection. The TCR Vβ repertoire of CD4+ T cells specific for the DR4-HCV 1248 complex in subjects 01-40 and 98A was analyzed. Fresh PBMC or short-term lines were enriched with the DR4-HCV 1248 tetramer and stained individually with a panel of 16 Vβ antibodies. In fresh PBMC from subject 01-40, 30% and 23% of DR4-HCV 1248+ cells were Vβ5.1+ and Vβ2+, respectively, indicating strong selection in vivo. A small population of tetramer+ cells (1.6%) was Vβ12+ ex vivo in subject 01-40; no other Vβ antibodies tested in this panel stained DR4-HCV 1248-positive cells, thus indicating that additional TCR Vβ segments were used by these HCV 1248-specific CD4+ T cells that were not detected here. Similar results were obtained with a short-term line from the same subject (FIGS. 12A-12B). A restricted TCR repertoire for the DR4-HCV 1248 complex was also observed in a short-term line from subject 98A since greater than 80% of CD4/DR4-HCV 1248+ cells were Vβ12+.

3. Example 3

This example illustrates another approach for using the present invention in a method for regulating an immune response in a subject. Specifically, MHC class II compounds are generated as described herein which are specific for a T cell antigen. These MHC class II compounds are administered in an effective amount to a subject in order to modulate the immune response.

4. Example 4

This example illustrates another approach for using the present invention in the treatment of an immune disorder in a subject. Specifically, MHC class II compounds are generated as described herein which are specific for an antigen of the immune disorder of interest. Examples include, but are not limited to, myelin basic protein (MBP), proteolipid protein (PLP) and/or myelin oligodendrocyte glycoprotein (MOG) for multiple sclerosis, preproinsulin, proinsulin, insulin, islet cell autoantigen IA-2 and/or GAD65 for type I diabetes. These complexes could be used for immunotherapy in autoimmune diseases since antibodies that bind to particular MHC/peptide complexes may permit selective depletion of antigen presenting cells that present the offending self-antigens. Using phage display technology as described in Krogsgaard, M. et al., all of the contents which are hereby incorporated by reference (Krogsgaard, M. et al. (2000) J. Exp. Med. 191:1395), peptide specific antibodies are produced which are specific for the MHC class II compounds identified.

Non-limiting examples of peptides that may be used to generate peptide-specific antibodies are as follows: for treatment of Type I diabetes, IA-2 (654-670) VSSVSSQFS-DAAQASPS (SEQ ID NO:22) (Peakman, M., et al. (1999) J Clin. Invest. 104:1449); proinsulin (73-90) GAGSLQPLA-LEGSLQKRG (SEQ ID NO:23) (Congia, M., et al. (1998) Proc. Natl. Acad. Sci., USA 95:3833); GAD65 (273-286) LIAFTSEHSHFSLK (SEQ ID NO:24); GAD65 (554-570) VNFFRMVISNPAATHQD (SEQ ID NO:25) (Nepom, G., et al. (2001) Proc. Natl. Acad Sci., USA 98:1763; for treatment of Multiple Sclerosis, MBP (85-99) ENPVVHFFKNIVTPR (SEQ ID NO:26); MBP (88-102) VVHFFKNIVTPRTPP (SEQ ID NO:27) (Wucherpfennig, K., et al. (1994) J. Exp. Med. 179:279); PLP (80-99) LYGALLLAEGFYT-TGAVRQI (SEQ ID NO:28); PLP (90-109) FYTTGAVR-QIFGDYKTTICG (SEQ ID NO:29); PLP (95-117) AVRQIF-GDYKTTICGKGLSATVT (SEQ ID NO:30); PLP (170-189) AVPVYIYFNTWTTCQSIAFP (SEQ ID NO:31); PLP (260-276) IAATYNFAVLKLMGRGTKF (SEQ ID NO:32) (Markovic-Plese, S., et al. (1995) J. Immunol. 155: 982); MOG (1-20) QFRVIGPRHPIRALVGDEV (SEQ ID NO:33); MOG (29-48) GKNATGMEVGWYRPPFSRVV (SEQ ID NO:34); MOG (39-58) WYRPPFSRVVH-LYRNGKDQD (SEQ ID NO:35) (identified based on the methods of the present invention).

These antibodies are administered in an effective amount to a patient in order to treat the disorder. The generation of antibodies is well known in the art. These antibodies can be administered during the course of disease for treatment (i.e., passive immunization) or may also be administered to a patient with a high risk of developing the disease prophylactically, i.e., before the onset of disease.

Moreover, the multimeric forms of the MHC class II compounds may also be used for the treatment of autoimmune diseases by targeting of T cell populations that cause the disease process. Specifically, MHC class II compounds are generated as described herein which are specific for a relevant T cell population. These MHC class II compounds are administered in an effective amount to a subject in order to treat the autoimmune disease. Dimeric forms (and possibly higher-order multimeric forms) of MHC class II compounds of the present invention are effective at inducing T cell anergy (see, e.g., Appel, H. et al. (2001) J. Immunol. 166:5279).

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. An isolated MHC class II compound comprising:
   (a) an MHC class II component comprising at least a portion of an MHC class II α chain and at least a portion of an MHC class II α chain, such that said MHC class II α chain and MHC class II α chain form a peptide binding groove;
   (b) a spaceholder molecule, wherein said spaceholder molecule:
      (1) consists of the amino acid sequence, PVSKMRMATPLLMQA (SEQ ID NO:1), and
      (2) is directly linked to a processable linker, wherein the processable linker is linked to said MHC class II component; and
   (c) an effector component, wherein said effector component is linked to said MHC class II component.

2. The MHC class II compound of claim 1, wherein said processable linker is linked to said MHC class II α chain of said MHC class II component.

3. The MHC class II compound of claim 1, wherein said effector component is linked to said MHC class II α chain of said MHC class II component by a second linker.

4. The MHC class II compound of claim 1, wherein said effector component is selected from the group consisting of a fluorescent label, biotin, at least part a portion of an immunoglobulin protein, a metallic compound, luciferin, a radiolabel, a cytokine, a viral capsid protein and an enzyme.

5. The method of claim 4, wherein said effector component is biotin.

6. The MHC class II compound of claim 1, wherein said MHC class II compound is encoded by a nucleic acid molecule, and wherein said nucleic acid molecule comprises a nucleic acid sequence encoding a signal segment attached to the N-terminus of said MHC class II component.

* * * * *

UNITED STATES PATENT AND TRADEMARK OFFICE
CERTIFICATE OF CORRECTION

| | | |
|---|---|---|
| PATENT NO. | : 8,314,210 B2 | Page 1 of 1 |
| APPLICATION NO. | : 10/617568 | |
| DATED | : November 20, 2012 | |
| INVENTOR(S) | : Wucherpfennig et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,560 days.

Signed and Sealed this
Eleventh Day of November, 2014

Michelle K. Lee
*Deputy Director of the United States Patent and Trademark Office*

SEQUENCE LISTING

<160> NUMBER OF SEQ ID NOS: 36

<210> SEQ ID NO 1
<211> LENGTH: 15
<212> TYPE: PRT
<213> ORGANISM: Homo sapiens

<400> SEQUENCE: 1

Pro Val Ser Lys Met Arg Met Ala Thr Pro Leu Leu Met Gln Ala
 1               5                  10                  15

<210> SEQ ID NO 2
<211> LENGTH: 13
<212> TYPE: PRT
<213> ORGANISM: Homo sapiens

<400> SEQUENCE: 2

Ala Ala Met Ala Ala Ala Ala Ala Ala Ala Met Ala Ala
 1               5                  10

<210> SEQ ID NO 3
<211> LENGTH: 13
<212> TYPE: PRT
<213> ORGANISM: Homo sapiens

<400> SEQUENCE: 3

Ala Ala Met Ala Ala Ala Ala Ala Ala Ala Ala Ala Ala
 1               5                  10

<210> SEQ ID NO 4
<211> LENGTH: 13
<212> TYPE: PRT
<213> ORGANISM: Homo sapiens

<400> SEQUENCE: 4

Ala Ala Phe Ala Ala Ala Ala Ala Ala Ala Ala Ala Ala
 1               5                  10

<210> SEQ ID NO 5
<211> LENGTH: 13
<212> TYPE: PRT
<213> ORGANISM: Homo sapiens

<400> SEQUENCE: 5

Ala Ser Met Ser Ala Ala Ser Ala Ala Ser Met Ala Ala
 1               5                  10

<210> SEQ ID NO 6
<211> LENGTH: 15
<212> TYPE: PRT
<213> ORGANISM: Homo sapiens

<400> SEQUENCE: 6

Gly Leu Asn Asp Ile Phe Glu Ala Gln Lys Ile Glu Trp His Glu
 1               5                  10                  15

<210> SEQ ID NO 7
<211> LENGTH: 6
<212> TYPE: PRT
<213> ORGANISM: Homo sapiens

<400> SEQUENCE: 7

Gly Gly Ser Gly Gly Ser
 1               5

<210> SEQ ID NO 8
<211> LENGTH: 19
<212> TYPE: PRT
<213> ORGANISM: Homo sapiens

<400> SEQUENCE: 8

Cys Gly Gly Gly Pro Val Ser Lys Met Arg Met Ala Thr Pro Leu Leu
 1               5                  10                  15

Met Gln Ala

<210> SEQ ID NO 9
<211> LENGTH: 17
<212> TYPE: PRT
<213> ORGANISM: Homo sapiens

<400> SEQUENCE: 9

Cys Gly Gly Gly Pro Lys Tyr Val Lys Gln Asn Thr Leu Lys Leu Ala
 1               5                  10                  15

Thr

<210> SEQ ID NO 10
<211> LENGTH: 13
<212> TYPE: PRT
<213> ORGANISM: Homo sapiens

<400> SEQUENCE: 10

Tyr Lys Arg Trp Ile Ile Leu Gly Leu Asn Lys Ile Val
 1               5                  10

<210> SEQ ID NO 11
<211> LENGTH: 13
<212> TYPE: PRT
<213> ORGANISM: Homo sapiens

<400> SEQUENCE: 11

Leu Asn Lys Ile Val Arg Met Tyr Ser Pro Thr Ser Ile
 1               5                  10

<210> SEQ ID NO 12
<211> LENGTH: 14
<212> TYPE: PRT
<213> ORGANISM: Homo sapiens

<400> SEQUENCE: 12

Ser Pro Glu Val Ile Pro Met Phe Ser Ala Leu Ser Glu Gly
 1               5                  10

<210> SEQ ID NO 13
<211> LENGTH: 14
<212> TYPE: PRT
<213> ORGANISM: Homo sapiens

<400> SEQUENCE: 13

Asp Arg Phe Tyr Lys Thr Leu Arg Ala Glu Gln Ala Ser Gln
 1               5                  10

<210> SEQ ID NO 14
<211> LENGTH: 15
<212> TYPE: PRT
<213> ORGANISM: Homo sapiens

<400> SEQUENCE: 14

Glu Gln Ile Gly Trp Met Thr Asn Asn Pro Pro Ile Pro Val Gly

-continued

```
                1               5              10              15

<210> SEQ ID NO 15
<211> LENGTH: 13
<212> TYPE: PRT
<213> ORGANISM: Homo sapiens

<400> SEQUENCE: 15

Pro Lys Tyr Val Lys Gln Asn Thr Leu Lys Leu Ala Thr
1               5                   10

<210> SEQ ID NO 16
<211> LENGTH: 16
<212> TYPE: PRT
<213> ORGANISM: Homo sapiens

<400> SEQUENCE: 16

Trp Asn Arg Gln Leu Tyr Pro Glu Trp Thr Glu Ala Gln Arg Leu Asp
1               5                   10                  15

<210> SEQ ID NO 17
<211> LENGTH: 16
<212> TYPE: PRT
<213> ORGANISM: Homo sapiens

<400> SEQUENCE: 17

Asp Val Pro Lys Trp Ile Ser Ile Met Thr Glu Arg Ser Val Pro His
1               5                   10                  15

<210> SEQ ID NO 18
<211> LENGTH: 15
<212> TYPE: PRT
<213> ORGANISM: Homo sapiens

<400> SEQUENCE: 18

Val Val His Phe Phe Lys Asn Ile Val Thr Pro Arg Thr Pro Pro
1               5                   10                  15

<210> SEQ ID NO 19
<211> LENGTH: 15
<212> TYPE: PRT
<213> ORGANISM: Homo sapiens

<400> SEQUENCE: 19

Gly Tyr Lys Val Leu Val Leu Asn Pro Ser Val Ala Ala Thr Leu
1               5                   10                  15

<210> SEQ ID NO 20
<211> LENGTH: 19
<212> TYPE: PRT
<213> ORGANISM: Homo sapiens

<400> SEQUENCE: 20

Ser Gly Glu Asn Leu Pro Tyr Leu Val Ala Tyr Gln Ala Thr Val Cys
1               5                   10                  15

Ala Arg Ala

<210> SEQ ID NO 21
<211> LENGTH: 21
<212> TYPE: PRT
<213> ORGANISM: Homo sapiens

<400> SEQUENCE: 21

Ser Gly Ile Gln Tyr Leu Ala Gly Leu Ser Thr Leu Pro Gly Asn Pro
1               5                   10                  15
```

Ala Ile Ala Ser Leu
            20

<210> SEQ ID NO 22
<211> LENGTH: 17
<212> TYPE: PRT
<213> ORGANISM: Homo sapiens

<400> SEQUENCE: 22

Val Ser Ser Val Ser Ser Gln Phe Ser Asp Ala Ala Gln Ala Ser Pro
1               5                   10                  15
Ser

<210> SEQ ID NO 23
<211> LENGTH: 18
<212> TYPE: PRT
<213> ORGANISM: Homo sapiens

<400> SEQUENCE: 23

Gly Ala Gly Ser Leu Gln Pro Leu Ala Leu Glu Gly Ser Leu Gln Lys
1               5                   10                  15
Arg Gly

<210> SEQ ID NO 24
<211> LENGTH: 14
<212> TYPE: PRT
<213> ORGANISM: Homo sapiens

<400> SEQUENCE: 24

Leu Ile Ala Phe Thr Ser Glu His Ser His Phe Ser Leu Lys
1               5                   10

<210> SEQ ID NO 25
<211> LENGTH: 17
<212> TYPE: PRT
<213> ORGANISM: Homo sapiens

<400> SEQUENCE: 25

Val Asn Phe Phe Arg Met Val Ile Ser Asn Pro Ala Ala Thr His Gln
1               5                   10                  15
Asp

<210> SEQ ID NO 26
<211> LENGTH: 15
<212> TYPE: PRT
<213> ORGANISM: Homo sapiens

<400> SEQUENCE: 26

Glu Asn Pro Val Val His Phe Phe Lys Asn Ile Val Thr Pro Arg
1               5                   10                  15

<210> SEQ ID NO 27
<211> LENGTH: 15
<212> TYPE: PRT
<213> ORGANISM: Homo sapiens

<400> SEQUENCE: 27

Val Val His Phe Phe Lys Asn Ile Val Thr Pro Arg Thr Pro Pro
1               5                   10                  15

<210> SEQ ID NO 28
<211> LENGTH: 20
<212> TYPE: PRT

<213> ORGANISM: Homo sapiens

<400> SEQUENCE: 28

Leu Tyr Gly Ala Leu Leu Ala Glu Gly Phe Tyr Thr Thr Gly Ala
1               5                   10                  15
Val Arg Gln Ile
            20

<210> SEQ ID NO 29
<211> LENGTH: 20
<212> TYPE: PRT
<213> ORGANISM: Homo sapiens

<400> SEQUENCE: 29

Phe Tyr Thr Thr Gly Ala Val Arg Gln Ile Phe Gly Asp Tyr Lys Thr
1               5                   10                  15
Thr Ile Cys Gly
            20

<210> SEQ ID NO 30
<211> LENGTH: 23
<212> TYPE: PRT
<213> ORGANISM: Homo sapiens

<400> SEQUENCE: 30

Ala Val Arg Gln Ile Phe Gly Asp Tyr Lys Thr Thr Ile Cys Gly Lys
1               5                   10                  15
Gly Leu Ser Ala Thr Val Thr
            20

<210> SEQ ID NO 31
<211> LENGTH: 20
<212> TYPE: PRT
<213> ORGANISM: Homo sapiens

<400> SEQUENCE: 31

Ala Val Pro Val Tyr Ile Tyr Phe Asn Thr Trp Thr Thr Cys Gln Ser
1               5                   10                  15
Ile Ala Phe Pro
            20

<210> SEQ ID NO 32
<211> LENGTH: 19
<212> TYPE: PRT
<213> ORGANISM: Homo sapiens

<400> SEQUENCE: 32

Ile Ala Ala Thr Tyr Asn Phe Ala Val Leu Lys Leu Met Gly Arg Gly
1               5                   10                  15
Thr Lys Phe

<210> SEQ ID NO 33
<211> LENGTH: 19
<212> TYPE: PRT
<213> ORGANISM: Homo sapiens

<400> SEQUENCE: 33

Gln Phe Arg Val Ile Gly Pro Arg His Pro Ile Arg Ala Leu Val Gly
1               5                   10                  15
Asp Glu Val

<210> SEQ ID NO 34

```
<211> LENGTH: 20
<212> TYPE: PRT
<213> ORGANISM: Homo sapiens

<400> SEQUENCE: 34

Gly Lys Asn Ala Thr Gly Met Glu Val Gly Trp Tyr Arg Pro Pro Phe
1               5                   10                  15

Ser Arg Val Val
            20

<210> SEQ ID NO 35
<211> LENGTH: 20
<212> TYPE: PRT
<213> ORGANISM: Homo sapiens

<400> SEQUENCE: 35

Trp Tyr Arg Pro Pro Phe Ser Arg Val Val His Leu Tyr Arg Asn Gly
1               5                   10                  15

Lys Asp Gln Asp
            20

<210> SEQ ID NO 36
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)
<223> OTHER INFORMATION: Xaa = Any Amino Acid
<220> FEATURE:
<221> NAME/KEY: MOD_RES
<222> LOCATION: (11)
<223> OTHER INFORMATION: Xaa = Any Amino Acid

<400> SEQUENCE: 36

Ala Ala Xaa Ala Ala Ala Ala Ala Ala Ala Xaa Ala Ala
1               5                   10
```